United States Patent
Ritzen et al.

(10) Patent No.: US 9,018,217 B2
(45) Date of Patent: Apr. 28, 2015

(54) PHENYLIMIDAZOLE DERIVATIVES AS PDE10A ENZYME INHIBITORS

(71) Applicant: H. Lundbeck A/S, Valby-Copenhagen (DK)

(72) Inventors: Andreas Ritzen, Copenhagen V. (DK); Morten Langgard, Glostrup (DK); Jan Kehler, Lyngby (DK); Jacob Nielsen, Copenhagen V. (DK); John Paul Kilburn, Haslev (DK); Mohamed M. Farah, Birmingham (GB)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/488,554

(22) Filed: Sep. 17, 2014

(65) Prior Publication Data
US 2015/0025081 A1     Jan. 22, 2015

Related U.S. Application Data

(60) Continuation of application No. 13/365,504, filed on Feb. 3, 2012, now Pat. No. 8,865,711, which is a division of application No. 12/487,694, filed on Jun. 19, 2009, now Pat. No. 8,133,897.

(60) Provisional application No. 61/171,523, filed on Apr. 22, 2009, provisional application No. 61/162,761, filed on Mar. 24, 2009, provisional application No. 61/074,226, filed on Jun. 20, 2008.

(51) Int. Cl.
| | |
|---|---|
| C07D 239/42 | (2006.01) |
| C07D 231/10 | (2006.01) |
| C07D 487/04 | (2006.01) |
| C07D 471/04 | (2006.01) |
| A61K 31/437 | (2006.01) |
| A61K 31/4985 | (2006.01) |
| A61K 45/06 | (2006.01) |

(52) U.S. Cl.
CPC ............ C07D 487/04 (2013.01); C07D 471/04 (2013.01); A61K 31/437 (2013.01); A61K 31/4985 (2013.01); A61K 45/06 (2013.01)

(58) Field of Classification Search
USPC ....................................... 514/256; 548/373.1
See application file for complete search history.

(56) References Cited

U.S. PATENT DOCUMENTS

| | | | |
|---|---|---|---|
| 4,036,840 | A | 7/1977 | O'Brien et al. |
| 7,897,619 | B2 | 3/2011 | Zeng et al. |
| 8,133,897 | B2 | 3/2012 | Ritzen et al. |
| 8,841,297 | B2 | 9/2014 | Ritzen et al. |
| 2008/0090891 | A1 | 4/2008 | Zelle |
| 2012/0135987 | A1 | 5/2012 | Ritzen et al. |

FOREIGN PATENT DOCUMENTS

| | | |
|---|---|---|
| TW | 2007/036246 A | 10/2007 |
| WO | 2004/005290 A1 | 1/2004 |
| WO | 2005/003129 A1 | 1/2005 |
| WO | 2005/082883 A2 | 9/2005 |
| WO | 2006/070284 A1 | 7/2006 |
| WO | 2007/077490 A2 | 7/2007 |
| WO | 2007/098169 A1 | 8/2007 |
| WO | 2008/001182 A1 | 1/2008 |
| WO | 2009/023179 A2 | 2/2009 |
| WO | 2010/145668 | 12/2010 |

OTHER PUBLICATIONS

Taiwan Examination report issued Jan. 13, 2014 in TW Application No. 098119876 filed Jun. 15, 2009.
International Search Report and Written Opinion issued Jul. 27, 2010 for International Application No. PCT/ DK2010/050147 filed Jun. 17, 2010.
Geyer et al., 2002, "Animal Models Relevant to Schizophrenia Disorders", Neuropsychopharmacology: The Fifth Generation of Progress, pp. 689-701.
Kehler, J., et al., 2007, "The potential therapeutic use of phosphodiesterase 10 inhibitors", Expert Opinion in Ther. Patents 17(2). p. 147-158.
CAS Registry No. 348125-42-8; Jul. 25, 2001.
CAS Registry No. 939690-18-3; Jun. 27, 2007.
CAS Registry No. 938887-78-6; Jun. 25, 2007.
CAS Registry No. 530154-74-6; Jun. 13, 2003.
CAS Registry No. 442570-89-0; Aug. 5, 2002.
CAS Registry No. 296791-07-6; Oct. 18, 2000.
International Search Report and Written Opinion issued Dec. 23, 2009 for International Application PCT/DK2009/050134 filed Jun. 19, 2009.

*Primary Examiner* — James O Wilson
*Assistant Examiner* — Oluwafemi Masha
(74) *Attorney, Agent, or Firm* — Mary Catherine Di Nunzio

(57) ABSTRACT

This invention is directed to compounds, which are PDE10A enzyme inhibitors. The invention provides a pharmaceutical composition comprising a therapeutically effective amount of a compound of the invention and a pharmaceutically acceptable carrier. The present invention also provides processes for the preparation of the compounds of formula I. The present invention further provides a method of treating a subject suffering from a neurodegenerative disorder comprising administering to the subject a therapeutically effective amount of a compound of formula I. The present invention also provides a method of treating a subject suffering from a drug addiction comprising administering to the subject a therapeutically effective amount of a compound of formula I. The present invention further provides a method of treating a subject suffering from a psychiatric disorder comprising administering to the subject a therapeutically effective amount of a compound of formula I.

29 Claims, No Drawings

PHENYLIMIDAZOLE DERIVATIVES AS PDE10A ENZYME INHIBITORS

CROSS-REFERENCE TO RELATED APPLICATIONS

The present application is a continuation of U.S. application Ser. No. 13/365,504, filed Feb. 3, 2012, which is a divisional of U.S. application Ser. No. 12/487,694, filed Jun. 19, 2009, now U.S. Pat. No. 8,133,897, which claims benefit of U.S. Provisional Application No. 61/171,523 filed Apr. 22, 2009, and claims priority of U.S. Provisional Application No. 61/162,761 filed Mar. 24, 2009, and claims benefit of U.S. Provisional Application No. 61/074,226 filed Jun. 20, 2008. Each of these applications is hereby incorporated by reference in its entirety.

FIELD OF THE INVENTION

The present invention provides compounds that are PDE10A enzyme inhibitors, and as such are useful to treat neurodegenerative and psychiatric disorders. Especially, the invention provides compounds that are highly selective for PDE10 over other PDE subtypes. The present invention also provides pharmaceutical compositions comprising compounds of the invention and methods of treating disorders using the compounds of the invention.

BACKGROUND OF THE INVENTION

Throughout this application, various publications are referenced in full. The disclosures of these publications are hereby incorporated by reference into this application to describe more fully the state of the art to which this invention pertains.

The cyclic nucleotides cyclic-adenosine monophosphate (cAMP) and cyclic-guanosine monophosphate (cGMP) function as intracellular second messengers regulating a vast array of processes in neurons. Intracellular cAMP and cGMP are generated by adenyl and guanyl cyclases, and are degraded by cyclic nucleotide phosphodiesterases (PDEs). Intracellular levels of cAMP and cGMP are controlled by intracellular signaling, and stimulation/repression of adenyl and guanyl cyclases in response to GPCR activation is a well characterized way of controlling cyclic nucleotide concentrations (Antoni, F. A. *Front. Neuroendocrinol.* 2000, 21, 103-132). cAMP and cGMP levels in turn control activity of cAMP- and cGMP-dependent kinases as well as other proteins with cyclic nucleotide response elements, which through subsequent phosphorylation of proteins and other processes regulate key neuronal functions such as synaptic transmission, neuronal differentiation and survival.

There are 21 phosphodiesterase genes that can be divided into 11 gene families. There are ten families of adenylyl cyclases, two of guanylyl cyclases, and eleven of phosphodiesterases. PDEs are a class of intracellular enzymes that regulate levels of cAMP and cGMP via hydrolysis of the cyclic nucleotides into their respective nucleotide monophosphates. Some PDEs degrade cAMP, some cGMP and some both. Most PDEs have a widespread expression and have roles in many tissues, while some are more tissue-specific.

Phosphodieasterase 10A (PDE10A) is a dual-specificity phosphodiesterase that can convert both cAMP to AMP and cGMP to GMP (Loughney, K. et al. *Gene* 1999, 234, 109-117; Fujishige, K. et al. *Eur. J. Biochem.* 1999, 266, 1118-1127 and Soderling, S. et al. *Proc. Natl. Acad. Sci.* 1999, 96, 7071-7076). PDE10A is primarily expressed in the neurons in the striatum, n. accumbens and in the olfactory tubercle (Kotera, J. et al. *Biochem. Biophys. Res. Comm.* 1999, 261, 551-557 and Seeger, T. F. et al. *Brain Research,* 2003, 985, 113-126).

Mouse PDE10A is the first identified member of the PDE10 family of phosphodiesterases (Fujishige, K. et al. *J. Biol. Chem.* 1999, 274, 18438-18445 and Loughney, K. et al. *Gene* 1999, 234, 109-117) and N-terminal splice variants of both the rat and human genes have been identified (Kotera, J. et al. *Biochem. Biophys. Res. Comm.* 1999, 261, 551-557 and Fujishige, K. et al. *Eur. J. Biochem.* 1999, 266, 1118-1127). There is a high degree of homology across species. PDE10A is uniquely localized in mammals relative to other PDE families. mRNA for PDE10 is highly expressed in testis and brain (Fujishige, K. et al. *Eur J Biochem.* 1999, 266, 1118-1127; Soderling, S. et al. *Proc. Natl. Acad. Sci.* 1999, 96, 7071-7076 and Loughney, K. et al. *Gene* 1999, 234, 109-117). These studies indicate that within the brain, PDE10 expression is highest in the striatum (caudate and putamen), n. accumbens and olfactory tubercle. More recently, an analysis has been made of the expression pattern in rodent brain of PDE10A mRNA (Seeger, T. F. et al. *Abst. Soc. Neurosci.* 2000, 26, 345.10) and PDE10A protein (Menniti, F. S. et al. William Harvey Research Conference 'Phosphodiesterase in Health and Disease', Porto, Portugal, Dec. 5-7, 2001).

PDE10A is expressed at high levels by the medium spiny neurons (MSN) of the caudate nucleus, the accumbens nucleus and the corresponding neurons of the olfactory tubercle. These constitute the core of the basal ganglia system. The MSN has a key role in the cortical-basal ganglia-thalamocortical loop, integrating convergent cortical/thalamic input, and sending this integrated information back to the cortex. MSN express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatel output pathway, which functions to suppress behavioral responses that compete with those being facilitated by the 'direct' pathway. These competing pathways act like the brake and accelerator in a car. In the simplest view, the poverty of movement in Parkinson's disease results from over-activity of the 'indirect' pathway, whereas excess movement in disorders such as Huntington's disease represent over-activity of the direct pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. *Brain Research,* 2003, 985, 113-126).

Dopamine $D_2$ receptor antagonism is well established in the treatment of schizophrenia. Since the 1950's, dopamine $D_2$ receptor antagonism has been the mainstay in psychosis treatment and all effective antipsychotic drugs antagonise $D_2$ receptors. The effects of $D_2$ are likely to be mediated primarily through neurons in the striatum, n. accumbens and olfactory tubercle, since these areas receive the densest dopaminergic projections and have the strongest expression of $D_2$ receptors (Konradi, C. and Heckers, S. *Society of Biological Psychiatry,* 2001, 50, 729-742). Dopamine $D_2$ receptor agonism leads to decrease in cAMP levels in the cells where it is expressed through adenylate cyclase inhibition, and this is a component of $D_2$ signalling (Stoof, J. C.; Kebabian J. W. *Nature* 1981, 294, 366-368 and Neve, K. A. et al. *Journal of Receptors and Signal Transduction* 2004, 24, 165-205). Conversely, $D_2$ receptor antagonism effectively increases cAMP levels, and this effect could be mimicked by inhibition of cAMP degrading phosphodiesterases.

Most of the 21 phosphodiesterase genes are widely expressed; therefore inhibition is likely to have side effects. Because PDE10A, in this context, has the desired expression profile with high and relatively specific expression in neurons in striatum, n. accumbens and olfactory tubercle, PDE10A inhibition is likely to have effects similar to $D_2$ receptor antagonism and therefore have antipsychotic effects.

While PDE10A inhibition is expected to mimic $D_2$ receptor antagonism in part, it might be expected to have a different profile. The $D_2$ receptor has signalling components besides cAMP (Neve, K. A. et al. *Journal of Receptors and Signal Transduction* 2004, 24, 165-205), wherefore interference with cAMP through PDE10A inhibition may negatively modulate rather than directly antagonise dopamine signaling through $D_2$ receptors. This may reduce the risk of the extrapyrimidal side effects that are seen with strong $D_2$ antagonism. Conversely, PDE10A inhibition may have some effects not seen with $D_2$ receptor antagonism. PDE10A is also expressed in $D_1$ receptors expressing striatal neurons (Seeger, T. F. et al. *Brain Research,* 2003, 985, 113-126). Since $D_1$ receptor agonism leads to stimulation of adenylate cyclase and resulting increase in cAMP levels, PDE10A inhibition is likely to also have effects that mimic $D_1$ receptor agonism. Finally, PDE10A inhibition will not only increase cAMP in cells, but might also be expected to increase cGMP levels, since PDE10A is a dual specificity phosphodiesterase. cGMP activates a number of target protein in cells like cAMP and also interacts with the cAMP signalling pathways. In conclusion, PDE10A inhibition is likely to mimic $D_2$ receptor antagonism in part and therefore has antipsychotic effect, but the profile might differ from that observed with classical $D_2$ receptor antagonists.

The PDE10A inhibitor papaverine is shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine induced hyperactivity was insignificant (WO 03/093499). These models suggest that PDE10A inhibition has the classic antipsychotic potential that would be expected from theoretical considerations. WO 03/093499 further discloses the use of selective PDE10 inhibitors for the treatment of associated neurologic and psychiatric disorders. Furthermore, PDE10A inhibition reverses subchronic PCP-induced deficits in attentional set-shifting in rats (Rodefer et al. *Eur. J. Neurosci.* 2005, 4, 1070-1076). This model suggests that PDE10A inhibition might alleviate cognitive deficits associated with schizophrenia.

The tissue distribution of PDE10A indicates that PDE10A inhibitors can be used to raise levels of cAMP and/or cGMP within cells that express the PDE10 enzyme, especially neurons that comprise the basal ganglia, and the PDE10A inhibitors of the present invention would therefore be useful in treating a variety of associated neuropsychiatric conditions involving the basal ganglia such as neurological and psychiatric disorders, schizophrenia, bipolar disorder, obsessive compulsive disorder, and the like, and may have the benefit of not possessing unwanted side effects, which are associated with the current therapies on the market.

Furthermore, recent publications (WO 2005/120514, WO 2005012485, Cantin et al, Bioorganic & Medicinal Chemistry Letters 17 (2007) 2869-2873) suggest that PDE10A inhibitors may be useful for treatment of obesity and non-insulin dependent diabetes.

With respect to inhibitors of PDE10A, EP 1250923 discloses the use of selective PDE10 inhibitors in general, and papaverine in particular, for the treatment of certain neurologic and psychiatric disorders.

WO 05/113517 discloses benzodiazepine stereospecific compounds as inhibitors of phosphodiesterase, especially types 2 and 4, and the prevention and treatment of pathologies involving a central and/or peripheral disorder. WO 02/88096 discloses benzodiazepine derivatives and their uses as inhibitors of phosphodiesterase, especially type 4 in the therapeutic field. WO 04/41258 discloses benzodiazepinone derivatives and their uses as inhibitors of phosphodiesterase, especially type 2 in the therapeutic field.

Pyrrdodihydroisoquinolines and variants thereof are disclosed as inhibitors of PDE10 in WO 05/03129 and WO 05/02579. Piperidinyl-substituted quinazolines and isoquinolines that serve as PDE10 inhibitors are disclosed in WO 05/82883. WO 06/11040 discloses substituted quinazoline and isoquinoline compounds that serve as inhibitors of PDE10. US 20050182079 discloses substituted tetrahydroisoquinolinyl derivatives of quinazoline and isoquinoline that serve as effective phosphodiesterase (PDE) inhibitors. In particular, US 20050182079 relates to said compounds, which are selective inhibitors of PDE10. Analogously, US 20060019975 discloses piperidine derivatives of quinazoline and isoquinoline that serve as effective phosphodiesterase (PDE) inhibitors. US 20060019975 also relates to compounds that are selective inhibitors of PDE10. WO 06/028957 discloses cinnoline derivatives as inhibitors of phosphodiesterase type 10 for the treatment of psychiatric and neurological syndromes.

However, these disclosures do not pertain to the compounds of the invention, which are structurally unrelated to any of the known PDE10 inhibitors (Kehler, J. et al. *Expert Opin. Ther. Patents* 2007, 17, 147-158), and which have now been found by the inventors to be highly active and selective PDE10A enzyme inhibitors.

The compounds 2-(5-Phenyl-1H-imidazol-2-ylmethylsulfanyl)-1H-benzoimidazole (CAS Registry no. 348125-42-8) and 2-(5-Phenyl-1H-imidazol-2-yl-sulfanylmethyl)-1H-benzoimidazole (CAS Registry no. 296791-07-6) appear in the chemical libraries of Scientific Exchange, Inc. and Zelinsky Institute of Organic Chemistry, respectively, but no pharmacological data appear to have been published. The compounds are both disclaimed from the scope of the present invention.

The compounds of the invention may offer alternatives to current marketed treatments for neurodegenerative and/or psychiatric disorders, which are not efficacious in all patients. Hence, there remains a need for alternative methods of treatment.

SUMMARY OF THE INVENTION

The objective of the present invention is to provide compounds that are selective PDE10A enzyme inhibitors.

A further objective of the present invention is to provide compounds which have such activity, and which have improved solubility, metabolic stability and/or bioavailability compared to prior art compounds.

Another objective of the invention is to provide an effective treatment, in particular long-term treatment, of a human patient, without causing the side effects typically associated with current therapies for neurological and psychiatric disorders.

Further objectives of the invention will become apparent upon reading the present specification.

Accordingly, in one aspect the present invention relates to compounds of formula I:

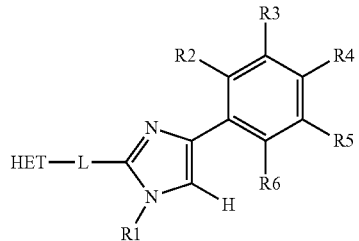

wherein HET is a heteroaromatic group of formula II containing from 2 to 4 nitrogen atoms:

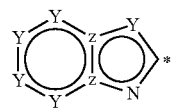

wherein Y can be N or CH, Z can be N or C, and wherein HET may optionally be substituted with up to three substituents R7, R8 and R9 individually selected from H; $C_1$-$C_6$ alkyl such as Me; halogen such as chlorine and bromine; cyano; halo ($C_1$-$C_6$)alkyl such as trifluoromethyl; aryl such as phenyl; alkoxy, preferably $C_1$-$C_6$ alkoxy, such as methoxy, dimethoxy, ethoxy, methoxy-ethoxy and ethoxy-methoxy, and $C_1$-$C_6$ hydroxyalkyl such as $CH_2CH_2OH$, and wherein * denotes the attachment point,
-L- is a linker selected from —S—$CH_2$—, —$CH_2$—S—, —$CH_2$—$CH_2$— or —CH=CH—,
R1 is selected from H; $C_1$-$C_6$ alkyl such as methyl, ethyl, 1-propyl, 2-propyl, isobutyl; $C_1$-$C_6$ alkyl($C_3$-$C_8$)cycloalkyl such as cyclopropylmethyl; $C_1$-$C_6$ hydroxyalkyl such as hydroxyethyl; $CH_2CN$; $CH_2C(O)NH_2$; $C_1$-$C_6$ arylalkyl such as benzyl and 4-chlorobenzyl; and $C_1$-$C_6$ alkyl-heterocycloalkyl such as tetrahydropyran-4-yl-methyl and 2-morpholin-4-yl-ethyl;
R2-R6 are each selected independently from H; $C_1$-$C_6$ alkoxy such as methoxy; and halogen such as chlorine or fluorine; and tautomers and pharmaceutically acceptable acid addition salts thereof, and polymorphic forms thereof, with the proviso that the compound is not 2-(5-Phenyl-1H-imidazol-2-ylmethylsulfanyl)-1H-benzoimidazole or 2-(5-Phenyl-1H-imidazol-2-yl-sulfanylmethyl)-1H-benzoimidazole In a particular embodiment, the invention relates to a compound of formula I in the form of a single tautomer or a polymorph.

In separate embodiments of the invention, the compound of formula I is selected among the specific compounds disclosed in the Experimental Section herein.

The invention further provides a compound of formula I, or a pharmaceutically acceptable acid addition salt thereof, for use as a medicament.

In another aspect, the present invention provides a pharmaceutical composition comprising a therapeutically effective amount of a compound of formula I and a pharmaceutically acceptable carrier, diluent or excipient.

The invention further provides the use of a compound of formula I, or a pharmaceutically acceptable acid addition salt thereof, for the preparation of a medicament for the treatment of a neurodegenerative or psychiatric disorder.

Furthermore, in yet another aspect, the present invention provides a method of treating a subject suffering from a neurodegenerative disorder, comprising administering to the subject a therapeutically effective amount of a compound of formula I. In a still further aspect, the present invention provides a method of treating a subject suffering from a psychiatric disorder, comprising administering to the subject a therapeutically effective amount of a compound of formula I. In another embodiment, the present invention provides a method of treating a subject suffering from a drug addiction, such as an alcohol, amphetamine, cocaine, or opiate addiction.

DETAILED DESCRIPTION OF THE INVENTION

Definition of Substitutents

As used in the context of the present invention, the terms "halo" and "halogen" are used interchangeably and refer to fluorine, chlorine, bromine or iodine.

The term "$C_1$-$C_6$ alkyl" refers to a straight-chain or branched saturated hydrocarbon having from one to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, and n-hexyl. The expression "$C_1$-$C_6$ hydroxyalkyl" refers to a $C_1$-$C_6$ alkyl group as defined above which is substituted with one hydroxy group. The term "halo($C_1$-$C_6$)alkyl" refers to a $C_1$-$C_6$ alkyl group as defined above which is substituted with up to three halogen atoms, such as trifluoromethyl.

The expression "$C_1$-$C_6$ alkoxy" refers to a straight-chain or branched saturated alkoxy group having from one to six carbon atoms, inclusive, with the open valency on the oxygen. Examples of such groups include, but are not limited to, methoxy, ethoxy, n-butoxy, 2-methyl-pentoxy and n-hexyloxy.

The term "$C_3$-$C_8$ cycloalkyl" typically refers to cyclopropyl, cyclobutyl, cyclopentyl, cyclohexyl, cycloheptyl or cyclooctyl. The expression "$C_1$-$C_6$ alkyl($C_3$-$C_8$)cycloalkyl" refers to a $C_3$-$C_6$ cycloalkyl as defined above which is substituted with a straight-chain or branched $C_1$-$C_6$ alkyl. Examples of such groups include, but are not limited to, cyclopropylmethyl.

The term "heterocycloalkyl" refers to a four to eight membered ring containing carbon atoms and up to three N, O or S atoms, provided that the four to eight membered ring does not contain adjacent O or adjacent S atoms. The open valency is on either the heteroatom or carbon atom. Examples of such groups include, but are not limited to, azetidinyl, oxetanyl, piperazinyl, morpholinyl, thiomorpholinyl and [1,4]diazepanyl. The term "hydroxyheterocycloalkyl" refers to a heterocycloalkyl as defined above which is substituted with one hydroxy group. The term "$C_1$-$C_6$ alkyl-heterocycloalkyl" refers to a heterocycloalkyl as defined above which is substituted with a $C_1$-$C_6$ alkyl group. Examples of such groups include, but are not limited to, tetrahydropyran-4-yl-methyl and 2-morpholin-4-yl-ethyl.

The term "aryl" refers to a phenyl ring, optionally substituted with halogen, $C_1$-$C_6$ alkyl, $C_1$-$C_6$ alkoxy or halo($C_1$-$C_6$) alkyl as defined above. Examples of such groups include, but are not limited to, phenyl and 4-chlorophenyl.

The term "$C_1$-$C_6$arylalkyl" refers to an aryl as defined above which is substituted with a straight-chain or branched $C_1$-$C_6$ alkyl. Examples of such groups include, but are not limited to, benzyl and 4-chlorobenzyl.

Additionally, the present invention further provides certain embodiments of the invention, which are described below.

In one embodiment of the invention, HET is a heteroaromatic group of formula II containing 2 nitrogen atoms. In another embodiment of the invention, HET is a heteroaromatic group of formula II containing 3 nitrogen atoms. In yet another embodiment of the invention, HET is a heteroaromatic group of formula II containing 4 nitrogen atoms.

HET is preferably chosen among the following heteroaromatic groups, wherein "*" denotes the attachment point:

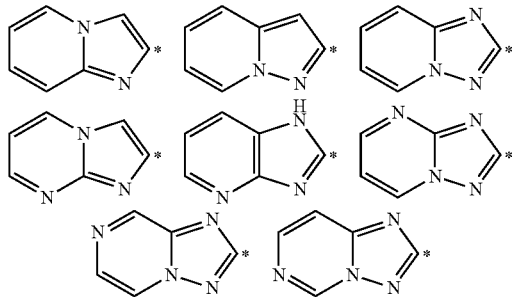

In a further embodiment, the heteroaromatic group HET is substituted with one substituent R7 selected from H; $C_1$-$C_6$ alkyl such as methyl; halogen such as chlorine or bromine; cyano; halo($C_1$-$C_6$)alkyl such as trifluoromethyl; aryl such as phenyl; and $C_1$-$C_6$ hydroxyalkyl such as $CH_2CH_2OH$. In another embodiment, HET is substituted with two substituents R7 and R8 individually selected from H; $C_1$-$C_6$ alkyl such as methyl; halogen such as chlorine or bromine; cyano; halo($C_1$-$C_6$)alkyl such as trifluoromethyl; aryl such as phenyl; and $C_1$-$C_6$ hydroxyalkyl such as $CH_2CH_2OH$. In a further embodiment, HET is substituted with three substituents R7, R8 and R9 individually selected from H; $C_1$-$C_6$ alkyl such as methyl; halogen such as chlorine or bromine; cyano; halo($C_1$-$C_6$)alkyl such as trifluoromethyl; aryl such as phenyl; and $C_1$-$C_6$ hydroxyalkyl such as $CH_2CH_2OH$.

In a specific embodiment, $R_7$, $R_8$ and $R_9$ are all hydrogen. In a different embodiment, at least one of $R_7$, $R_8$ and $R_9$ is $C_1$-$C_6$ alkyl such as methyl. In a further embodiment, at least one of $R_7$, $R_8$ and $R_9$ is halogen such as chlorine or bromine.

Specific embodiments of the compound for which the HET radical is derived are given below.

In a specific embodiment, HET is imidazo[1,2-a]pyrimidine. In a second specific embodiment, HET is [1,2,4]triazolo[1,5-a]pyridine. In a third specific embodiment, HET is imidazo[1,2-a]pyridine. In a fourth specific embodiment, HET is imidazo[4,5-b]pyrimidine. In a fifth specific embodiment, HET is pyrazolo[1,5-a]pyridine. In a sixth specific embodiment, HET is [1,2,4]Triazolo[1,5-a]pyrimidine. In a seventh specific embodiment, HET is [1,2,4]Triazolo[1,5-c]pyrimidine. In an eight specific embodiment, HET is [1,2,4]Triazolo[1,5-a]pyrazine.

In another specific embodiment, HET is [1,2,4]triazolo[1,5-a]pyrimidine. In another specific embodiment, HET is [1,2,4]triazolo[1,5-a]pyridine-6-carbonitrile. In another specific embodiment, HET is 1-methyl-1H-benzoimidazole. In another specific embodiment, HET is 1-phenyl-1H-benzoimidazole. In another specific embodiment, HET is 2-(6-chloro-benzoimidazol-1-yl)-ethanol. In another specific embodiment, HET is 5,7-dimethyl-[1,2,4]triazolo[1,5-a]pyridine. In another specific embodiment, HET is 5,7-dimethyl-imidazo[1,2-a]pyridine. In another specific embodiment, HET is 5-chloro-imidazo[1,2-a]pyridine. In another specific embodiment, HET is 5-methyl-imidazo[1,2-a]pyridine. In another specific embodiment, HET is 5-trifluoromethyl-imidazo[1,2-a]pyridine. In another specific embodiment, HET is 6-Bromo-5,7-dimethyl-[1,2,4]triazolo[1,5-a]pyridine. In another specific embodiment, HET is 6-bromo-7-methyl-[1,2,4]triazolo[1,5-a]pyridine. In another specific embodiment, HET is 6-chloro-8-methyl-[1,2,4]triazolo[1,5-a]pyridine. In another specific embodiment, HET is 6-chloro-imidazo[1,2-a]pyridine. In another specific embodiment, HET is 7-methyl-[1,2,4]triazolo[1,5-a]pyridine. In another specific embodiment, HET is 8-methyl-imidazo[1,2-a]pyridine. In another specific embodiment, HET is imidazo[1,2-a]pyridine-7-carbonitrile. In another specific embodiment, HET is 5,7-Dimethyl-[1,2,4]triazolo[1,5-a]pyrimidine.

Typically, HET is 5,7-dimethyl-imidazo[1,2-a]pyrimidine or [1,2,4]Triazolo[1,5-c]pyrimidine or [1,2,4]Triazolo[1,5-a]pyrazine.

In another embodiment of the invention, -L- is —S—$CH_2$—. In a further embodiment, -L- is —$CH_2$—S—. In yet another embodiment, -L- is —$CH_2$—$CH_2$—. In a still further embodiment, -L- is —CH═CH—.

In a further embodiment of the invention, $R_1$ is H. In another embodiment, $R_1$ is $C_1$-$C_6$ straight or branched chain alkyl. In another embodiment, $R_1$ is $C_1$-$C_6$ hydroxyalkyl. In another embodiment, $R_1$ is $C_1$-$C_6$ alkyl($C_3$-$C_6$)cycloalkyl. In a further embodiment, $R_1$ is $C_1$-$C_6$ alkyl-heterocycloalkyl. In another embodiment, $R_1$ is $C_1$-$C_6$ arylalkyl. In a further embodiment, $R_1$ is $CH_2CN$. In a still further embodiment, $R_1$ is $CH_2C(O)NH_2$.

In a specific embodiment, $R_1$ is methyl. In another specific embodiment, $R_1$ is ethyl. In another specific embodiment, $R_1$ is 1-propyl. In another specific embodiment, $R_1$ is 2-propyl. In another specific embodiment, $R_1$ is isobutyl. In another specific embodiment, $R_1$ is hydroxyethyl. In another specific embodiment, $R_1$ is cyclopropylmethyl. In another specific embodiment, $R_1$ is tetrahydropyran-4-yl-methyl. In another specific embodiment, $R_1$ is 2-morpholin-4-yl-ethyl. In another specific embodiment, $R_1$ is benzyl. In another specific embodiment, $R_1$ is 4-chlorobenzyl. In another specific embodiment, $R_1$ is $CH_2CN$. In another specific embodiment, $R_1$ is $CH_2C(O)NH_2$.

In one embodiment of the invention, $R_2$, $R_3$, $R_4$, $R_5$ and $R_6$ are all hydrogen. In another embodiment, at least one of $R_2$, $R_3$, $R_4$, $R_5$ and $R_6$ is $C_1$-$C_6$ alkoxy such as methoxy. In a further embodiment of the invention, at least one of $R_2$, $R_3$, $R_4$, $R_5$ and $R_6$ is halogen such as chlorine or fluorine.

In one embodiment of the invention, $R_2$ is hydrogen. In another embodiment, $R_2$ is $C_1$-$C_6$ alkoxy such as methoxy. In a further embodiment, $R_2$ is halogen such as chlorine or fluorine.

In one embodiment of the invention, $R_3$ is hydrogen. In another embodiment, $R_3$ is $C_1$-$C_6$ alkoxy such as methoxy. In a further embodiment, $R_3$ is halogen such as chlorine or fluorine.

In one embodiment of the invention, $R_4$ is hydrogen. In another embodiment, $R_4$ is $C_1$-$C_6$ alkoxy such as methoxy. In a further embodiment, $R_4$ is halogen such as chlorine or fluorine.

In one embodiment of the invention, $R_5$ is hydrogen. In another embodiment, $R_5$ is $C_1$-$C_6$ alkoxy such as methoxy. In a further embodiment, $R_5$ is halogen such as chlorine or fluorine.

In one embodiment of the invention, $R_6$ is hydrogen. In another embodiment, $R_6$ is $C_1$-$C_8$ alkoxy such as methoxy. In a further embodiment, $R_6$ is halogen such as chlorine or fluorine.

It should be understood that the various aspects, embodiments, implementations and features of the invention mentioned herein may be claimed separately, or in any combination, as illustrated by the following non-limiting examples:

In a specific embodiment, HET is 5,7-Dimethyl-imidazo[1,2-a]pyrimidine; -L- is —S—CH2- or —CH2-S—; $R_1$ is selected from hydrogen, methyl, 1-propyl, isobutyl, cyclopropylmethyl, benzyl and 2-morpholin-4-yl-ethyl; and $R_2$-$R_6$ are all hydrogen.

In another specific embodiment, HET is selected from 5,7-dimethyl-imidazo[1,2-a]pyrimidine, 5,7-dimethyl-[1,2,4]triazolo[1,5-a]pyridine, 5,7-Dimethyl-[1,2,4]triazolo[1,5-a]pyrimidine, 5-trifluoromethyl-imidazo[1,2-a]pyridine, [1,2,4]triazolo[1,5-a]pyridine and 6-chloro-8-methyl-[1,2,4]triazolo[1,5-a]pyridine; -L- is selected from —S—CH2-, —CH2-S— and —CH2CH2-; $R_1$ is selected from hydrogen, methyl, ethyl, 2-propyl, $CH_2CN$ and tetrahydropyran-4-yl-methyl; and $R_2$-$R_6$ are all hydrogen.

In separate embodiments of the invention, the compound of formula I is selected among the following specific compounds, in the form of the free base, one or more tautomers thereof or a pharmaceutically acceptable acid addition salt thereof. Table 1 lists compounds of the invention and the corresponding $IC_{50}$ values determined as described in the section "PDE10A inhibition assay". Each of the compounds constitutes an individual embodiment, of the present invention:

TABLE 1

Compounds of the invention and $IC_{50}$ values

| Compound | IC50 (nM) |
|---|---|
| 5,7-Dimethyl-2-[1-(3-methyl-butyl)-4-phenyl-1H-imidazol-2-ylsulfanylmethyl]-imidazo[1,2-a]pyrimidine | 5.4 |
| 5,7-Dimethyl-2-(4-phenyl-1-propyl-1H-imidazol-2-ylsulfanylmethyl)-imidazo[1,2-a]pyrimidine | 9.1 |
| 2-(1-Cyclopropylmethyl-4-phenyl-1H-imidazol-2-ylsulfanylmethyl)-5,7-dimethyl-imidazo[1,2-a]pyrimidine | 12 |
| 5,7-dimethyl-2((1-methyl-4-phenyl-1H-imidazol-2-ylthio)methyl)imidazo[1,2-a]pyrimidine | 20 |
| 5,7-Dimethyl-2-[1-(2-morpholin-4-yl-ethyl)-4-phenyl-1H-imidazol-2-ylsulfanylmethyl]-imidazo[1,2-a]pyrimidine | 22 |
| 5,7-Dimethyl-2-(1-methyl-4-phenyl-1H-imidazol-2-ylsulfanylmethyl)-[1,2,4]triazolo[1,5-a]pyridine | 26 |
| 2-(1-Cyclopropylmethyl-4-phenyl-1H-imidazol-2-ylmethylsulfanyl)-5,7-dimethyl-[1,2,4]triazolo[1,5-a]pyridine | 34 |
| 2-(1-Benzyl-4-phenyl-1H-imidazol-2-ylmethylsulfanyl)-5,7-dimethyl-[1,2,4]triazolo[1,5-a]pyridine | 48 |
| [2-(5,7-Dimethyl-imidazo[1,2-a]pyrimidin-2-ylmethylsulfanyl)-4-phenyl-imidazol-1-yl]-acetonitrile | 52 |
| 5,7-Dimethyl-2-[4-phenyl-1-(tetrahydro-pyran-4-ylmethyl)-1H-imidazol-2-ylsulfanylmethyl]-imidazo[1,2-a]pyrimidine | 59 |
| 5,7-Dimethyl-2-(1-methyl-4-phenyl-1H-imidazol-2-ylmethylsulfanyl)-[1,2,4]triazolo[1,5-a]pyridine | 61 |
| 5,7-Dimethyl-2-(4-phenyl-1H-imidazol-2-ylmethylsulfanyl)-[1,2,4]triazolo[1,5-a]pyridine | 64 |
| 2-(1-Methyl-4-phenyl-1H-imidazol-2-ylsulfanylmethyl)-5-trifluoromethyl-imidazo[1,2-a]pyridine | 66 |
| 2-(1-Ethyl-4-phenyl-1H-imidazol-2-ylmethylsulfanyl)-5,7-dimethyl-[1,2,4]triazolo[1,5-a]pyridine | 68 |
| 5,7-Dimethyl-2-[2-(1-methyl-4-phenyl-1H-imidazol-2-yl)-ethyl]-imidazo[1,2-a]pyrimidine | 68 |
| [2-(5,7-Dimethyl-[1,2,4]triazolo[1,5-a]pyridin-2-ylsulfanylmethyl)-4-phenyl-imidazol-1-yl]-acetonitrile | 69 |
| 2-(1-Isopropyl-4-phenyl-1H-imidazol-2-ylmethylsulfanyl)-5,7-dimethyl-[1,2,4]triazolo[1,5-a]pyridine | 70 |
| 2-(1-Methyl-4-phenyl-1H-imidazol-2-ylmethylsulfanyl)-[1,2,4]triazolo[1,5-a]pyridine | 75 |
| 2-(1-Benzyl-4-phenyl-1H-imidazol-2-ylsulfanylmethyl)-5,7-dimethyl-imidazo[1,2-a]pyrimidine | 84 |
| 2-(4-Phenyl-1H-imidazol-2-ylmethylsulfanyl)-[1,2,4]triazolo[1,5-a]pyridine | 87 |

TABLE 1-continued

Compounds of the invention and $IC_{50}$ values

| Compound | IC50 (nM) |
|---|---|
| 6-Chloro-8-methyl-2-(1-methyl-4-phenyl-1H-imidazol-2-ylmethylsulfanyl)-[1,2,4]triazolo[1,5-a]pyridine | 91 |
| trans-5,7-Dimethyl-2-[(E)-2-(1-methyl-4-phenyl-1H-imidazol-2-yl)-vinyl]-imidazo[1,2-a]-pyrimidine | 92 |
| 2-(1-Isopropyl-4-phenyl-1H-imidazol-2-ylsulfanylmethyl)-5,7-dimethyl-imidazo[1,2-a]pyrimidine | 92 |
| 2-[4-(3-Fluoro-phenyl)-1-methyl-1H-imidazol-2-ylmethylsulfanyl]-5,7-dimethyl-[1,2,4]triazolo[1,5-a]pyridine | 100 |
| 2-(1-Ethyl-4-phenyl-1H-imidazol-2-ylsulfanylmethyl)-5,7-dimethyl-imidazo[1,2-a]pyrimidine | 100 |
| 2-(5,7-Dimethyl-imidazol[1,2-a]pyrimidin-2-ylmethylsulfanyl)-4-phenyl-imidazol-1-ylamine | 110 |
| 5,7-Dimethyl-2-(1-methyl-4-phenyl-1H-imidazol-2-ylsulfanylmethyl)-imidazo[1,2-a]pyrimidine | 140 |
| 2-[4-(3-Methoxy-phenyl)-1-methyl-1H-imidazol-2-ylmethylsulfanyl]-5,7-dimethyl-[1,2,4]triazolo[1,5-a]pyridine | 170 |
| 7-Methyl-2-(1-methyl-4-phenyl-1H-imidazol-2-ylmethylsulfanyl)-[1,2,4]triazolo[1,5-a]pyridine | 170 |
| 2-[4-(3-Chloro-phenyl)-1-methyl-1H-imidazol-2-ylmethylsulfanyl]-5,7-dimethyl-[1,2,4]triazolo[1,5-a]pyridine | 180 |
| 2-[4-(4-Fluoro-phenyl)-1-methyl-1H-imidazol-2-ylmethylsulfanyl]-5,7-dimethyl-[1,2,4]triazolo[1,5-a]pyridine | 180 |
| 2-[2-(5,7-Dimethyl-[1,2,4]triazolo[1,5-a]pyridin-2-ylsulfanylmethyl)-4-phenyl-imidazol-1-yl]-acetamide | 210 |
| 2-[4-(3-Methoxy-phenyl)-1-methyl-1H-imidazol-2-ylmethylsulfanyl]-5,7-dimethyl-imidazo[1,2-a]pyrimidine | 210 |
| 5-Chloro-2-(1-methyl-4-phenyl-1H-imidazol-2-ylsulfanylmethyl)-imidazo[1,2-a]pyridine | 220 |
| 8-Methyl-2-(1-methyl-4-phenyl-1H-imidazol-2-ylsulfanylmethyl)-imidazo[1,2-a]pyridine | 230 |
| 2-[4-(2-Fluoro-phenyl)-1-methyl-1H-imidazol-2-ylmethylsulfanyl]-5,7-dimethyl-[1,2,4]triazolo[1,5-a]pyridine | 240 |
| 2-[4-(2-Chloro-phenyl)-1-methyl-1H-imidazol-2-ylmethylsulfanyl]-5,7-dimethyl-[1,2,4]triazolo[1,5-a]pyridine | 250 |
| 2-[2-(5,7-Dimethyl-imidazol[1,2-a]pyrimidin-2-yrmethylsulfanyl)-4-phenyl-imidazol-1-yl]-acetamide | 250 |
| 2-(1-Ethyl-4-phenyl-1H-imidazol-2-ylmethylsulfanyl)-[1,2,4]triazolo[1,5-a]pyridine | 260 |
| 2-(1-Methyl-4-phenyl-1H-imidazol-2-ylmethylsulfanyl)-1-phenyl-1H-benzoimidazole | 330 |
| 2-[4-(2-Methoxy-phenyl)-1-methyl-1H-imidazol-2-ylmethylsulfanyl]-5,7-dimethyl-[1,2,4]triazolo[1,5-a]pyridine | 330 |
| 2-(1-Methyl-4-phenyl-1H-imidazol-2-ylsulfanylmethyl)-imidazo[1,2-a]pyridine-7-carbonitrile | 360 |
| 2-(1-Isopropyl-4-phenyl-1H-imidazol-2-ylmethylsulfanyl)-[1,2,4]triazolo[1,5-a]pyridine | 380 |
| 2-[1-(4-Chloro-benzyl)-4-phenyl-1H-imidazol-2-ylmethylsulfanyl]-5,7-dimethyl-[1,2,4]triazolo[1,5-a]pyridine | 410 |
| 6-Bromo-5,7-dimethyl-2-(1-methyl-4-phenyl-1H-imidazol-2-ylmethylsulfanyl)-[1,2,4]triazo[1,5-a]pyridine | 420 |
| 2-[4-(3-Fluoro-phenyl)-1-methyl-1H-imidazol-2-ylmethylsulfanyl]-[1,2,4]triazolo[1,5-a]pyridine | 430 |
| 2-(1-Methyl-4-phenyl-1H-imidazol-2-ylsulfanylmethyl)-pyrazolo[1,5-a]pyridine | 430 |
| 5-Methyl-2-(1-methyl-4-phenyl-1H-imidazol-2-ylsulfanylmethyl)-imidazo[1,2-a]pyridine | 480 |
| 2-[4-(4-Fluoro-phenyl)-1-methyl-1H-imidazol-2-ylmethylsulfanyl]-[1,2,4]triazolo[1,5-a]pyridine | 570 |
| 2-(1-Methyl-4-phenyl-1H-imidazol-2-ylsulfanylmethyl)-1-phenyl-1H-benzoimidazole | 580 |
| 2-[4-(3-Chloro-phenyl)-1-methyl-1H-imidazol-2-ylmethylsulfanyl]-[1,2,4]triazolo[1,5-a]pyridine | 810 |
| 2-(6-Chloro-imidazo[1,2-a]pyridin-2-ylmethylsulfanyl)-4-phenyl-imidazol-1-ylamine | 830 |
| 2-(1-Methyl-4-phenyl-1H-imidazol-2-ylmethylsulfanyl)-1H-imidazo[4,5-b]pyridine | 840 |
| 6-Chloro-8-methyl-2-(1-methyl-4-phenyl-1H-imidazol-2-ylsulfanylmethyl)-imidazo[1,2-a]pyridine | 890 |
| 2-[4-(4-Chloro-phenyl)-1-methyl-1H-imidazol-2-ylmethylsulfanyl]-5,7-dimethyl-[1,2,4]triazolo[1,5-a]pyridine | 1100 |
| 6-Bromo-7-methyl-2-(1-methyl-4-phenyl-1H-imidazol-2-ylmethylsulfanyl)-[1,2,4]triazolo[1,5-a]pyridine | 1200 |
| 2-(1-Methyl-4-phenyl-1H-imidazol-2-ylsulfanylmethyl)-[1,2,4]triazolo[1,5-a]pyrimidine | 1500 |

TABLE 1-continued

Compounds of the invention and IC$_{50}$ values

| Compound | IC50 (nM) |
|---|---|
| 2-[2-(1-Amino-4-phenyl-1H-imidazol-2-ylsulfanylmethyl)-6-chloro-benzoimidazol-1-yl]-ethanol | 1500 |
| 2-(Imidazo[1,2-a]pyridin-2-ylmethylsulfanyl)-4-phenyl-imidazol-1-ylamine | 1500 |
| 2-(1-Methyl-4-phenyl-1H-imidazol-2-ylsulfanylmethyl)-imidazo[1,2-a]pyridine | 1500 |
| 2-(1-Methyl-4-phenyl-1H-imidazol-2-ylmethylsulfanyl)-[1,2,4]triazolo[1,5-a]pyridine-6-carbonitrile | 1600 |
| 2-[4-(4-Methoxy-phenyl)-1-methyl-1H-imidazol-2-ylmethylsulfanyl]-5,7-dimethyl-[1,2,4]triazolo[1,5-a]pyridine | 1600 |
| 1-Methyl-2-(1-methyl-4-phenyl-1H-imidazol-2-ylmethylsulfanyl)-1H-benzoimidazole | 1800 |
| 2-(1-Methyl-4-phenyl-1H-imidazol-2-ylsulfanylmethyl)-imidazo[1,2-a]pyrimidine | 2900 |
| 8-Methyl-2-(4-phenyl-1H-imidazol-2-ylsulfanylmethyl)-imidazo[1,2-a]pyridine | 370 |
| 2-[1-(4-Chloro-benzyl)-4-phenyl-1H-imidazol-2-ylsulfanylmethyl]-5,7-dimethyl-imidazo[1,2-a]pyrimidine | 470 |
| 4-(2-(2-((8-chloro-[1,2,4]triazolo[1,5-a]pyridin-2-yl)methylthio)-4-phenyl-1H-imidazol-1-ypethyl)morpholine | 17 |
| 8-Methyl-2-[2-(1-methyl-4-phenyl-1H-Imidazol-2-yl)-ethyl]-[1,2,4]triazolo[1,5-a]pyridine | 12 |
| 8-Methyl-2-{2-[1-(2-morpholin-4-yl-ethyl)-4-phenyl-1H-imidazol-2-yl]-ethyl}-1H-1,2,4]triazolo[1,5-a]pyridine | 8.1 |
| 5-Methyl-2-[2-(1-methyl-4-phenyl-1H-imidazol-2-yl)-ethyl]-[1,2,4]triazolo[1,5-a]pyridine | 14 |
| 5-Methyl-2-{2-[1-(2-morpholin-4-yl-ethyl)-4-phenyl-1H-imidazol-2-yl]-ethyl}-[1,2,4]triazolo[1,5-a]pyridine | 8.1 |
| 4-(2-(2-((5-chloro-[1,2,4]triazolo[1,5-a]pyridin-2-yl)methylthio)-4-phenyl-1H-imidazol-1-yl)ethyl)morpholine | 33 |
| 5,7-dimethyl-2-(2-(1-methyl-4-phenyl-1H-imidazol-2-yl)ethyl)-[1,2,4]triazolo[1,5-a]pyridine | 17 |
| 4-(2-(2-(2-(5,7-dimethyl-[1,2,4]triazolo[1,5-a]pyridin-2-yl)ethyl)-4-phenyl-1H-imidazol-1-yl)ethyl)morpholine | 6 |
| 6,8-dimethyl-2-(2-(1-methyl-4-phenyl-1H-imidazol-2-yl)ethyl)-[1,2,4]triazolo[1,5-a]pyridine | 19 |
| 5,7-Dimethyl-2-[2-(4-phenyl-1H-imidazol-2-yl)ethyl]-[1,2,4]triazolo[1,5-a]pyricline | 15 |
| 5,7-Dimethyl-2-[2-(1-methyl-4-phenyl-1H-imidazol-2-yl)-ethyl]-[1,2,4]triazolo[1,5-a]pyrimidine | 12 |
| 2-(2-(1-ethyl-4-phenyl-1H-imidazol-2-yl)ethyl)-5,7-dimethyl-[1,2,4]triazolo[1,5-a]pyridine | 36 |
| 5,7-dimethyl-2-(2-(4-phenyl-1-propyl-1H-imidazol-2-yl)ethyl)-[1,2,4]triazolo[1,5-a]pyridine | 26 |
| 5,7-Dimethyl-2-[2-(4-phenyl-1H-imidazol-2-yl)-ethyl]-[1,2,4]triazolo[1,5-a]pyrimidine | 5.3 |
| 5,7-Dimethyl-2-(4-phenyl-1H-imidazol-2-ylsulfanylmethyl)-[1,2,4]triazolo[1,5-a]pyrimidine | 24 |
| 5,8-Dimethyl-2-[2-(1-methyl-4-phenyl-1H-imidazol-2-yl)-ethyl]-[1,2,4]triazolo[1,5-a]pyridine | 0.32 |
| 5,7-Dimethyl-2-(1-methyl-4-phenyl-1H-imidazol-2-ylsulfanylmethyl)-[1,2,4]triazolo[1,5-a]pyridine | 25 |
| 5-Methyl-2-[2-(4-phenyl-1H-imidazol-2-yl)-ethyl]-[1,2,4]triazolo[1,5-a]pyridine | 2.8 |
| 2-(1-Isobutyl-4-phenyl-1H-imidazol-2-ylsulfanylmethyl)-5,7-dimethyl-[1,2,4]triazolo[1,5-a]pyrimidine | 4.2 |
| 5,7-Dimethyl-2-[1-(2-morpholin-4-yl-ethyl)-4-phenyl-1H-imidazol-2-ylsulfanylmethyl]-[1,2,4]triazolo[1,5-a]pyrimidine | 5 |
| 5-Methyl-2-[2-(1-methyl-4-phenyl-1H-imidazol-2-yl)-ethyl]-7-morpholin-4-yl-[1,2,4]triazolo[1,5-a]pyrimidine | 6.9 |
| 2-[2-(1-Isobutyl-4-phenyl-1H-imidazol-2-yl)-ethyl]-5-methyl-[1,2,4]triazolo[1,5-a]pyrimidine | 1.6 |
| 2-[2-(1-Isopropyl-4-phenyl-1H-imidazol-2-yl)-ethyl]-5-methyl-[1,2,4]triazolo[1,5-a]pyrimidine | 23 |
| 1-Methyl-3-(2-[2-[2-(5-methyl-[1,2,4]triazolo[1,5-a]pyridin-2-yl)-ethyl]-4-phenyl-1H-imidazol-1-yl)-ethyl)-imidazolidin-2-one | 2.8 |
| 5-Methyl-2-{2-[4-phenyl-1-(3-piperidin-1-yl-propyl)-1H-imidazol-2-yl]-ethyl}-[1,2,4]triazolo[1,5-a]pyridine | 25 |
| Diisopropyl-(2-[2-[2-(5-methyl-[1,2,4]triazolo[1,5-a]pyridin-2-yl)-ethyl]-4-phenyl-imidazol-1-yl}-ethyl)-amine | 7.3 |
| 8-Methoxy-2-(1-methyl-4-phenyl-1H-imidazol-2-ylsulfanylmethyl)-[1,2,4]triazolo[1,5-a]pyridine | 40 |
| 1-{2-[2-(5,7-Dimethyl-[1,2,4]triazolo[1,5-a]pyrimidin-2-ylmethylsulfanyl)-4-phenyl-imidazol-1-yl]-ethyl}-3-methyl-imidazolidin-2-one | 25 |
| 5,6,7-Trimethyl-2-[2-(1-methyl-4-phenyl-1H-imidazol-2-yl)-ethyl]-[1,2,4]triazolo[1,5-a]pyrimidine | 15 |
| 5-Methyl-2-[2-(1-methyl-4-phenyl-1H-imidazol-2-yl)-ethyl]-7-phenyl-[1,2,4]triazolo[1,5-a]pyrimidine | 2.8 |
| 5-Methyl-2-(2-[4-phenyl-1-(2-piperidin-1-yl-ethyl)-1H-imidazol-2-yl]-ethyl}-[1,2,4]triazolo[1,5-a]pyridine | 1.3 |
| 2-[4-(3-Methoxy-phenyl)-1-methyl-1H-imidazol-2-ylmethylsulfanyl]-5,7-dimethyl-[1,2,4]triazolo[1,5-a]pyrimidine | 80 |
| 5-Ethyl-2-(1-methyl-4-phenyl-1H-imidazol-2-ylsulfanylmethyl)-[1,2,4]triazolo[1,5-a]pyridine | 7.5 |
| 5,7-Dimethyl-2-(1-methyl-4-phenyl-1H-imidazol-2-ylmethylsulfanyl)-[1,2,4]triazolo[1,5-a]pyrimidine | 120 |
| 5,7-Dimethyl-2-{2-[4-phenyl-1-(2-piperidin-1-yl-ethyl)-1H-imidazol-2-yl]-ethyl}-[1,2,4]triazolo[1,5-a]pyrimidine | 2.7 |
| 2-[2-(1-Isobutyl-4-phenyl-1H-imidazol-2-yl)-ethyl]-5,7-dimethyl-[1,2,4]triazolo[1,5-a]pyrimidine | 1.3 |
| 2-[2-(1-Isopropyl-4-phenyl-1H-imidazol-2-yl)-ethyl]-5,7-dimethyl-[1,2,4]triazolo[1,5-a]pyrimidine | 3.4 |
| 1-(2-[2-[2-(5,7-Dimethyl-[1,2,4]triazolo[1,5-a]pyrimidin-2-yl)-ethyl]-4-phenyl-imidazol-1-yl}-3-methyl-imidazolidin-2-one | 4.4 |
| (2-{2-[2-(5,7-Dimethyl-[1,2,4]triazolo[1,5-a]pyrimidin-2-yl)-ethyl]-4-phenyl-imidazol-1-yl}-ethyl)-diisopropyl-amine | 8.7 |
| 5,7-Dimethyl-2-{2-[1-(2-morpholin-4-yl-ethyl)-4-phenyl-1H-imidazol-2-yl]-ethyl}-[1,2,4]triazolo[1,5-a]pyrimidine | 1.4 |
| 5,7-Dimethyl-2-[2-(4-phenyl-1-propyl-1H-imidazol-2-yl)-ethyl]-[1,2,4]triazolo[1,5-a]ayridine | 0.69 |
| 1-[2-[2-(5,7-Dimethyl-[1,2,4]triazolo[1,5-a]pyrimidin-2-yl)-ethyl]-4-phenyl-imidazol-1-yl]-propan-2-ol | 13 |
| (S)-1-{2-[2-(5,7-Dimethyl-[1,2,4]triazolo[1,5-a]pyrimidin-2-yl)-ethyl]-4-phenyl-imidazol-1-yl}-propan-2-ol | 5.5 |
| 8-methoxy-5-methyl-2-(2-(1-methyl-4-phenyl-1H-imidazol-2-yl)ethyl)-[1,2,4]triazolo[1,5-a]ayridine | 2.5 |
| (R)-1-[2-[2-(5,7-Dimethyl-[1,2,4]triazolo[1,5-a]pyrimidin-2-yl)-ethyl]-4-phenyl-imidazol-1-yl]-propan-2-ol | 11 |
| 8-fluoro-2-(2-(1-methyl-4-phenyl-1H-imidazol-2-yl)ethyl)-[1,2,4]triazolo[1,5-a]pyridine | 120 |
| 1-{2-[2-(5,7-Dimethyl]-[1,2,4]triazolo[1,5-a]pyrimidin-2-yl)-ethyl]-4-phenyl-imidazol-1-yl}-2-methyl-propan-2-ol | 29 |
| 8-Ethyl-5-methyl-2-(2-(1-methyl-4-phenyl-1H-imidazol-2-yl)-ethyl)-[1,2,4]triazolo[1,5-c]pyrimidine | 1.1 |
| 5-Methyl-2-[2-(1-methyl-4-phenyl-1H-imidazol-2-yl)-ethyl]-7-propyl-[1,2,4]triazolo[1,5-a]pyrimidine | 3.6 |
| 5,8-Dimethyl-2-[2-(1-methyl-4-phenyl-1H-imidazol-2-yl)-ethyl]-[1,2,4]triazolo[1,5-a]pyrazine | 1.8 |
| 7-Methoxy-5-methyl-2-[2-(1-methyl-4-phenyl-1H-imidazol-2-yl)-ethyl]-[1,2,4]triazolo[1,5-c]pyrimidine | 160 |
| 7-Isopropyl-5-methyl-2-[2-(1-methyl-4-phenyl-1H-imidazol-2-yl)-ethyl]-[1,2,4]triazolo[1,5-a]pyrimidine | 4.8 |
| 2-{2-[4-(2,4-Difluoro-phenyl)-1-methyl-1H-imidazol-2-yl]-ethyl}-5,7-dimethyl-[1,2,4]triazolo[1,5-a]pyrimidine | 79 |
| 7-Methoxy-5,8-dimethyl-2-[2-(1-methyl-4-phenyl-1H-imidazol-2-yl)-ethyl]-[1,2,4]triazolo[1,5-c]pyrimidine | 29 |
| 5,8-Dimethyl-2-[2-(1-methyl-4-phenyl-1H-imidazol-2-yl)-ethyl]-[1,2,4]triazolo[1,5-c]pyrimidine | 7.2 |
| 2-{2-[4-(2-Methoxy-phenyl)-1-methyl-1H,imidazol-2-yl]-ethyl)-5,7-dimethyl-[1,2,4]triazolo[1,5-a]pyrimidine | 32 |
| {5-Methyl-2-[2-(1-methyl-4-phenyl-1H-imidazol-2-yl)-ethyl]-[1,2,4]triazolo[1,5-a]pyrimidin-7-yl}-methanol | 15 |
| 8-Ethyl-5-methyl-2-[2-(1-methyl-4-phenyl-1H-imidazol-2-yl)-ethyl]-[1,2,4]triazolo[1,5-a]pyridine | 0.93 |
| 5,8-Dimethoxy-2-[2-(1-methyl-4-phenyl-1H-imidazol-2-yl)-ethyl]-[1,2,4]triazolo[1,5-a]pyridine | 33 |

In a particular embodiment of the present invention the compounds of the present invention have an IC$_{50}$ value of less than 50 nM, such as in the range of 0.2-20 nM, particularly in the range of 0.2-10 nM, such as in the range of 0.2-5 nM or in the range of 0.2-1 nM.

Selected compounds have been tested for their ability to reverse phencyclidine (PCP) induced hyperactivity. The reversal of the PCP effect is measured as described in the section "Phencyclidine (PCP) induced hyperactivity".

Results of the experiments showed that the tested compounds of the invention are in vivo active compounds that reverse the PCP induced hyperactivity to the % shown in the table.

TABLE 2

Reversal of PCP induced hyperactivity

| Compound | % reversal of PCP induced hyperactivity |
|---|---|
| 8-Methyl-2-[2-(1-methyl-4-phenyl-1H-imidazol-2-yl)-ethyl]-[1,2,4]triazolo[1,5-a]pyridine | 69 |
| 5-Methyl-2-[2-(1-methyl-4-phenyl-1H-imidazol-2-yl)-ethyl]-[1,2,4]triazolo[1,5-a]pyridine | 66 |
| 5,7-Dimethyl-2-[2-(1-methyl-4-phenyl-1H-imidazol-2-yl)-ethyl]-[1,2,4]triazolo[1,5-a]pyrimidine | 84 |
| 5,7-Dimethyl-2-[2-(4-phenyl-1H-imidazol-2-yl)-ethyl]-[1,2,4]triazolo[1,5-a]pyrimidine | 38 |
| 5,8-Dimethyl-2-[2-(1-methyl-4-phenyl-1H-imidazol-2-yl)-ethyl]-[1,2,4]triazolo[1,5-a]pyridine | 67 |
| 5-Methyl-2-[2-(1-methyl-4-phenyl-1H-imidazol-2-yl)-ethyl]-7-morpholin-4-yl-[1,2,4]triazolo[1,5-a]pyrimidine | 17 |
| Diisopropyl-(2-{2-[2-(5-methyl-[1,2,4]triazolo[1,5-a]pyridin-2-yl)-ethyl]-4-phenyl-imidazol-1-yl}-ethyl)-amine | 27 |
| 8-Methoxy-2-(1-methyl-4-phenyl-1H-imidazol-2-ylsulfanylmethyl)-[1,2,4]triazolo[1,5-a]pyridine | 26 |
| 5,6,7-Trimethyl-2-[2-(1-methyl-4-phenyl-1H-imidazol-2-yl)-ethyl]-[1,2,4]triazolo[1,5-a]pyrimidine | 14 |
| 2-[4-(3-Methoxy-phenyl)-1-methyl-1H-imidazol-2-ylmethylsulfanyl]-5,7-dimethyl-[1,2,4]triazolo[1,5-a]pyrimidine | 36 |
| (2-{2-[2-(5,7-Dimethyl-[1,2,4]triazolo[1,5-a]pyrimidin-2-yl)-ethyl]-4-phenyl-imidazol-1-yl}-ethyl)-diisopropyl-amine | 14 |
| 5,7-Dimethyl-2-[2-(4-phenyl-1-propyl-1H-imidazol-2-yl)-ethyl]-[1,2,4]triazolo[1,5-a]pyrimidine | 3 |
| 1-{2-[2-(5,7-Dimethyl-[1,2,4]triazolo[1,5-a]pyrimidin-2-yl)-ethyl]-4-phenyl-imidazol-1-yl}-propan-2-ol | 15 |
| 8-methoxy-5-methyl-2-(2-(1-methyl-4-phenyl-1H-imidazol-2-yl)ethyl)-[1,2,4]triazolo[1,5-a]pyridine | 57 |
| 1-{2-[2-(5,7-Dimethyl-[1,2,4]triazolo[1,5-a]pyrimidin-2-yl)-ethyl]-4-phenyl-imidazol-1-yl)-2-methyl-propan-2-ol | 33 |
| 8-Ethyl-5-methyl-2-[2-(1-methyl-4-phenyl-1H-imidazol-2-yl)-ethyl]-[1,2,4]triazolo[1,5-c]pyrimidine | 85 |
| 5,8-Dimethyl-2-[2-(1-methyl-4-phenyl-1H-imidazol-2-yl)-ethyl]-[1,2,4]triazolo[1,5-a]pyrazine | 99 |
| 7-Isopropyl-5-methyl-2-[2-(1-methyl-4-phenyl-1H-imidazol-2-yl)-ethyl]-[1,2,4]triazolo[1,5-a]pyrimidine | 30 |
| 7-Methoxy-5,8-dimethyl-2-[2-(1-methyl-4-phenyl-1H-imidazol-2-yl)-ethyl]-[1,2,4]triazolo[1,5-c]pyrimidine | 41 |
| 5,8-Dimethyl-2-[2-(1-methyl-4-phenyl-1H-imidazol-2-yl)-ethyl]-[1,2,4]triazolo[1,5-c]pyrimidine | 96 |
| 8-Ethyl-5-methyl-2-[2-(1-methyl-4-phenyl-1H-imidazol-2-yl)-ethyl]-[1,2,4]triazolo[1,5-a]pyridine | 31 |

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Serge, S. M. et al., *J. Pharm. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Compositions

The present invention further provides a pharmaceutical composition comprising a therapeutically effective amount of a compound of formula I and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of formula I and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound having the utility of a free base. When a compound of formula I contains a free base such salts are prepared in a conventional manner by treating a solution or suspension of a free base of formula I with a molar equivalent of a pharmaceutically acceptable acid. Representative examples of suitable organic and inorganic acids are described above.

For parenteral administration, solutions of the compounds of formula I in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula I may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula I and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Treatment of Disorders

As mentioned above, the compounds of formula I are PDE10A enzyme inhibitors and as such are useful to treat associated neurological and psychiatric disorders.

The invention thus provides a compound of formula I or a pharmaceutically acceptable acid addition salt thereof, as well as a pharmaceutical composition containing such a compound, for use in the treatment of a neurodegenerative disorder, psychiatric disorder or drug addiction in mammals including humans; wherein the neurodegenerative disorder is selected from the group consisting of Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline; and wherein the psychiatric disorder is selected from the group consisting of schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type; and wherein the drug addiction is an alcohol, amphetamine, cocaine, or opiate addiction.

The compounds of formula I or pharmaceutically acceptable salts thereof may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefore, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The present invention provides a method of treating a mammal, including a human, suffering from a neurodegenerative disorder selected from a cognition disorder or movement disorder, which method comprises administering to the subject a therapeutically effective amount of a compound of formula I.

This invention further provides a method of treating a neurodegenerative disorder or condition in a mammal, including a human, which method comprises administering to said mammal an amount of a compound of formula I effective in inhibiting PDE10.

This invention also provides a method of treating a subject suffering from a psychiatric disorder, which method comprises administering to the subject a therapeutically effective amount of a compound of formula I. Examples of psychiatric disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type; and the anxiety disorder is selected from panic disorder; agoraphobia; a specific phobia; social phobia; obsessive-compulsive disorder; post-traumatic stress disorder; acute stress disorder; and generalized anxiety disorder.

It has been found that the compounds of formula I or pharmaceutically acceptable salts thereof may advantageously be administered in combination with at least one neuroleptic agent (which may be a typical or an atypical antipsychotic agent) to provide improved treatment of psychiatric disorders such as schizophrenia. The combinations, uses and methods of treatment of the invention may also provide advantages in treatment of patients who fail to respond adequately or who are resistant to other known treatments.

The present invention thus provides a method of treating a mammal suffering from a psychiatric disorder, such as schizophrenia, which method comprises administering to the mammal a therapeutically effective amount of a compound of formula I, either alone or as combination therapy together with at least one neuroleptic agent.

The term "neuroleptic agent" as used herein refers to drugs, which have the effect on cognition and behaviour of antipsychotic agent drugs that reduce confusion, delusions, hallucinations, and psychomotor agitation in patients with psychoses. Also known as major tranquilizers and antipsychotic drugs, neuroleptic agents include, but are not limited to: typical antipsychotic drugs, including phenothiazines, further divided into the aliphatics, piperidines, and piperazines, thioxanthenes (e.g., cisordinol), butyrophenones (e.g., haloperidol), dibenzoxazepines (e.g., loxapine), dihydroindolones (e.g., molindone), diphenylbutylpiperidines (e.g., pimozide), and atypical antipsychotic drugs, including benzisoxazoles (e.g., risperidone), sertindole, olanzapine, quetiapine, osanetant and ziprasidone.

Particularly preferred neuroleptic agents for use in the invention are sertindole, olanzapine, risperidone, quetiapine, aripiprazole, haloperidol, clozapine, ziprasidone and osanetant.

The present invention further provides a method of treating a subject suffering from a cognition disorder, which method comprises administering to the subject a therapeutically effective amount of a compound of formula I. Examples of cognition disorders that can be treated according to the present invention include, but are not limited to, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

This invention also provides a method of treating a movement disorder, which method comprises administering to the subject a therapeutically effective amount of a compound of formula I. Examples of movement disorders that can be treated according to the present invention include, but are not limited to, Huntington's disease and dyskinesia associated with dopamine agonist therapy. This invention further provides a method of treating a movement disorder selected from Parkinson's disease and restless leg syndrome, which comprises administering to the subject a therapeutically effective amount of a compound of formula I.

This invention also provides a method of treating a mood disorder, which method comprises administering to the subject a therapeutically effective amount of a compound of formula I. Examples of mood disorders and mood episodes that can be treated according to the present invention include, but are not limited to, major depressive episode of the mild, moderate or severe type, a manic or mixed mood episode, a hypomanic mood episode; a depressive episode with a typical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder. It is understood that a mood disorder is a psychiatric disorder.

This invention further provides a method of treating a drug addiction, for example an alcohol, amphetamine, cocaine, or opiate addiction, in a mammal, including a human, which method comprises administering to said mammal an amount of a compound of formula I effective in treating drug addiction.

This invention also provides a method of treating a drug addiction, for example an alcohol, amphetamine, cocaine, or opiate addiction, in a mammal, including a human, which method comprises administering to said mammal an amount of a compound of formula I effective in inhibiting PDE10.

The term "drug addiction", as used herein, means an abnormal desire for a drug and is generally characterized by motivational disturbances such a compulsion to take the desired drug and episodes of intense drug craving.

Drug addiction is widely considered a pathological state. The disorder of addiction involves the progression of acute drug use to the development of drug-seeking behavior, the vulnerability to relapse, and the decreased, slowed ability to respond to naturally rewarding stimuli. For example, The Diagnostic and Statistical Manual of Mental Disorders, Fourth Edition (DSM-IV) has categorized three stages of addiction: preoccupation/anticipation, binge/intoxication, and withdrawal/negative affect. These stages are characterized, respectively, everywhere by constant cravings and preoccupation with obtaining the substance; using more of the substance than necessary to experience the intoxicating effects; and experiencing tolerance, withdrawal symptoms, and decreased motivation for normal life activities.

This invention further provides a method of treating a disorder comprising as a symptom a deficiency in attention and/or cognition in a mammal, including a human, which method comprises administering to said mammal an amount of a compound of formula I effective in treating said disorder.

Other disorders that can be treated according to the present invention are obsessive/compulsive disorders, Tourette's syndrome and other tic disorders.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temporal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the present invention, the neurodegenerative disorder or condition involves neurodegeneration of striatal medium spiny neurons in a mammal, including a human.

In a further embodiment of the present invention, the neurodegenerative disorder or condition is Huntington's disease.

In another embodiment, the invention provides a method of treating a subject to reduce body fat or body weight, or to treat non-insuline demanding diabetes mellitus (NIDDM), metabolic syndrome, or glucose intolerance, comprising administering to a subject in need thereof a therapeutically effective amount of a compound of formula I. In preferred embodiments, the subject is human, the subject is overweight or obese and the antagonist is administered orally. In another preferred embodiment, the method further comprising administering a second therapeutic agent to the subject, preferably an anti-obesity agent, e.g., rimonabant, orlistat, sibutramine, bromocriptine, ephedrine, leptin, pseudoephedrine, or peptide YY3-36, or analogs thereof.

The term "metabolic syndrome" as used herein refers to a constellation of conditions that place people at high risk for coronary artery disease. These conditions include type 2 diabetes, obesity, high blood pressure, and a poor lipid profile with elevated LDL ("bad") cholesterol, low HDL ("good") cholesterol, and elevated triglycerides. All of these conditions are associated with high blood insulin levels. The fundamental defect in the metabolic syndrome is insulin resistance in both adipose tissue and muscle.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Experimental Section

Preparation of the Compounds of the Invention

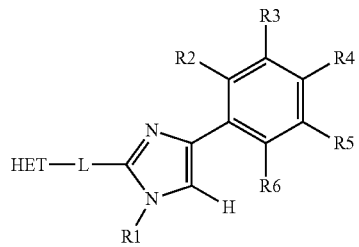

Compounds of the general formula I of the invention may be prepared as described in the following reaction schemes. Unless otherwise indicated, in the reaction schemes and discussion that follow, HET, $R_1$-$R_9$, -L-, Z and Y are as defined above.

Compounds of formula I, wherein -L- is —S—$CH_2$—, can be prepared by the coupling of a nucleophile of formula III or IIIa with an electrophile of formula IV, where X is a leaving group, e.g. Cl, Br, I, methanesulfonyl, 4-toluenesulfonyl, as shown in scheme 1. In the reaction between IIIa and IV, alkylation of the sulfur atom of IIIa with IV and ring closure to form the triazole ring both take place under the same reaction conditions in a one-pot procedure.

Scheme 1.

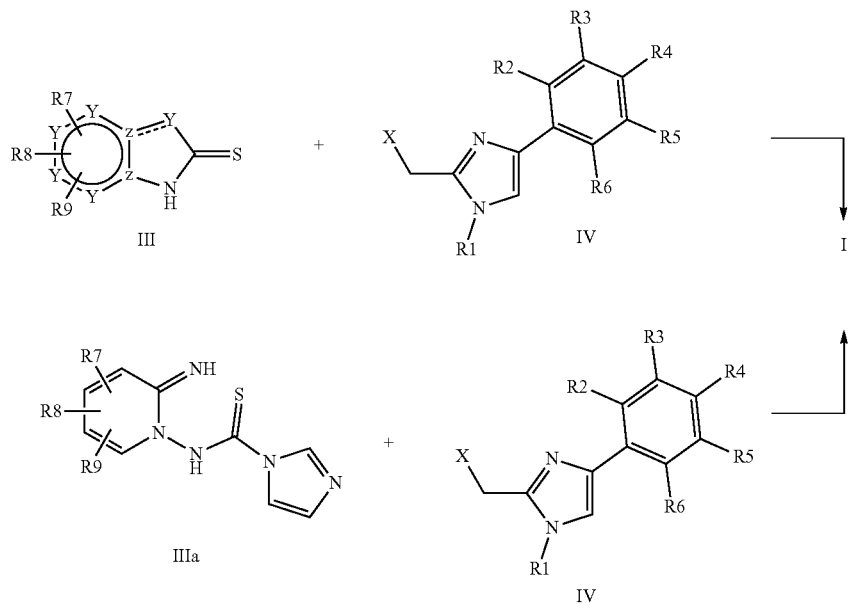

This reaction is typically carried out in a solvent such as 1-propanol, toluene, DMF, or acetonitrile, optionally in the presence of a carbonate base such as potassium carbonate or a tertiary amine base such as triethylamine or diisopropylethylamine (DIPEA), at a temperature ranging from about 0° C. to about 200° C., optionally under pressure in a closed vessel. Other suitable solvents include benzene, chloroform, dioxane, ethyl acetate, 2-propanol and xylene. Alternatively, solvent mixtures such as toluene/2-propanol can be used.

Compounds of formula III are either commercially available or can be prepared as described in the literature, see for example Brown et al. *Aust. J. Chem.* 1978, 31, 397-404; Yutilov et al. *Khim. Geter. Soedin.* 1988, 799-804; Wiide et al. *Bioorg. Med. Chem. Lett.* 1995, 5, 167-172; Kidwai et al. *J. Korean Chem. Soc.* 2005, 49, 288-291. Compounds of formula IIIa can be prepared as described in WO 96/01826 from the corresponding 1,2-diaminopyridines by reaction with thiocarbonyldiimidazote in a suitable solvent, such as chloroform, at a suitable temperature, such as room temperature or +40° C. The requisite 1,2-diaminopyridines are readily available from the corresponding commercially available 2-aminopyridines by reaction with a suitable N-amination reagent, such as O-(mesitylsulfonyl)hydroxylamine, in a suitable solvent, such as chloroform, at a suitable temperature, such as 0° C. or room temperature, see WO 96/01826.

2-Halomethyl-4-(aryl)-1H-imidazoles of formula IV can be prepared by halogenation of the corresponding 2-hydroxymethyl-4-(aryl)-1H-imidazoles using a suitable reagent, e.g. thionyl chloride, phosphorous trichloride, or phosphorous tribromide, optionally using a suitable solvent such as dichloromethane, using methods well known to chemists skilled in the art. The requisite 2-hydroxymethyl-4-(aryl)-1H-imidazoles can be prepared by methods known in the art (see for example Magdolen, P; Vasella, A. *Helv. Chim. Acta* 2005, 88, 2454-2469; Song, Z. et al. *J. Org. Chem.* 1999, 64, 1859-1867).

Compounds of formula I, wherein -L- is —CH$_2$—S—, can be prepared by the coupling of a nucleophile of formula X with an electrophile of formula VI as shown in scheme 2.

Scheme 2.

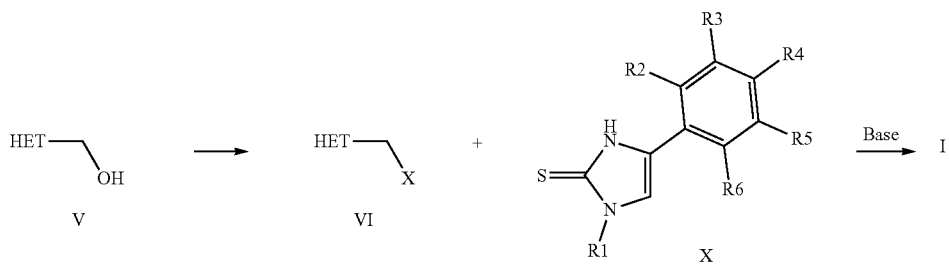

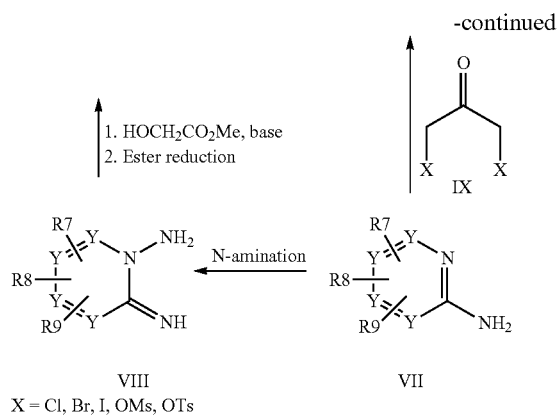

X = Cl, Br, I, OMs, OTs

This reaction is typically carried out in a solvent such as 1-propanol, toluene, DMF, or acetonitrile, optionally in the presence of a carbonate base such as potassium carbonate or a tertiary amine base such as triethylamine or diisopropylethylamine (DIPEA), at a temperature ranging from about 0° C. to about 200° C., optionally under pressure in a closed vessel. Other suitable solvents include benzene, chloroform, dioxane, ethyl acetate, 2-propanol and xylene. Alternatively, solvent mixtures such as toluene/2-propanol can be used.

Some electrophiles of formula VI are commercially available, and many others are known in the art, see for example JP 59176277. The electrophile VI, where X is a leaving group, e.g. Cl, Br, I, methanesulfonyl, 4-toluenesulfonyl, can also be prepared by conversion of the primary alcohol of compounds of formula V to said leaving group by methods known to chemists skilled in the art. Said methods can for example be selected from reacting compounds of formula V with thionyl chloride, phosphorous trichloride, phosphorous tribromide, methanesulfonyl chloride, or 4-toluenesulfonyl chloride optionally in the presence of a suitable solvent, such as dichloromethane or 1,2-dichloroethane, and optionally in the presence of a base, such as triethylamine, diisopropylethylamine, or pyridine. Alternatively, electrophiles of formula VI can be prepared by reacting commercially available aromatic amines of formula VII with 1,3-dihaloacetones of formula IX, e.g. 1,3-dichloroacetone, in a suitable solvent, such as 1,2-dimethoxyethane or ethanol, at a suitable temperature, such as room temperature or reflux. Some electrophiles of formula V are commercially available, and many others are known in the art, see for example Tsuchiya, T.; Sashida, H. *J. Chem. Soc., Chem. Commun.* 1980, 1109-1110; Tsuchiya, T.; Sashida, H; Konoshita, A. *Chem. Pharm. Bull.* 1983, 31, 4568-4572. Alternatively, alcohols of formula V can be prepared by reacting commercially available aromatic amines of formula VII with a suitable N-amination reagent, such as O-(mesitylsulfonyl)hydroxylamine, in a suitable solvent, such as chloroform, at a suitable temperature, such as 0° C. or room temperature, see WO 96/01826, to yield compounds of formula VIII. Said compounds of formula VIII can be converted into compounds of formula V by reaction with methyl glycolate followed by reduction of the methyl ester to the requisite alcohol using a suitable reducing agent such as lithium aluminium hydride in a suitable solvent such as diethyl ether or tetrahydrofuran using methods known to chemists skilled in the art.

Compounds of formula X are either commercially available or can be prepared as described in the literature, see e.g. Kjellin, G; Sandström, J. *Acta Chem. Scand.* 1969, 23, 2879-2887; Laufer, S. A. et al. *Synthesis* 2008, 253-266.

Compounds of formula I, wherein R1 is not hydrogen, can be prepared by the alkylation of a compounds of formula I, wherein R1 is hydrogen, with an alkyl halide of formula XI as shown in scheme 3.

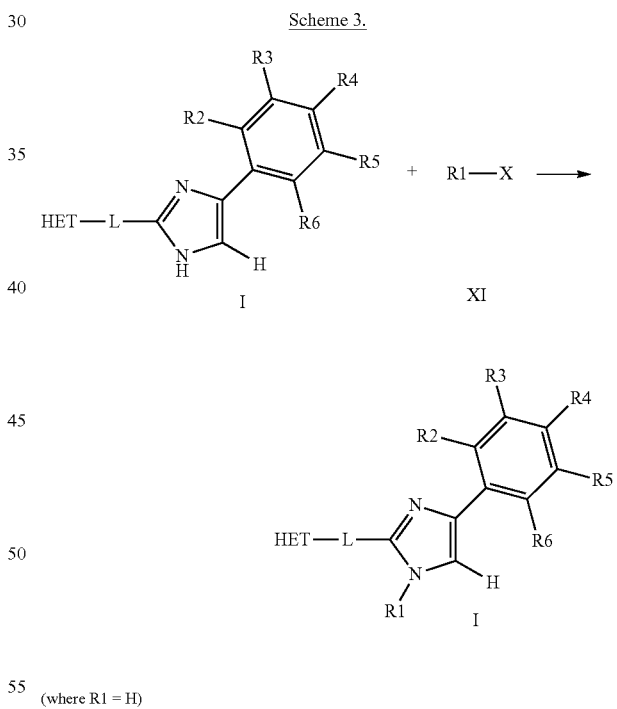

Scheme 3.

(where R1 = H)

This reaction is typically carried out in a suitable solvent, such as dimethylformamide, dimethylacetamide, or acetonitrile, in the presence of a suitable base such as a carbonate base, e.g. potassium carbonate, or a tertiary amine base, e.g. triethylamine or diisopropylethylamine (DIPEA), at a temperature ranging from about 0° C. to about 100° C.

Compounds of formula I, wherein -L- is —CH═CH— or —CH$_2$—CH$_2$— can be prepared by the reaction sequence shown in scheme 4.

Scheme 4.

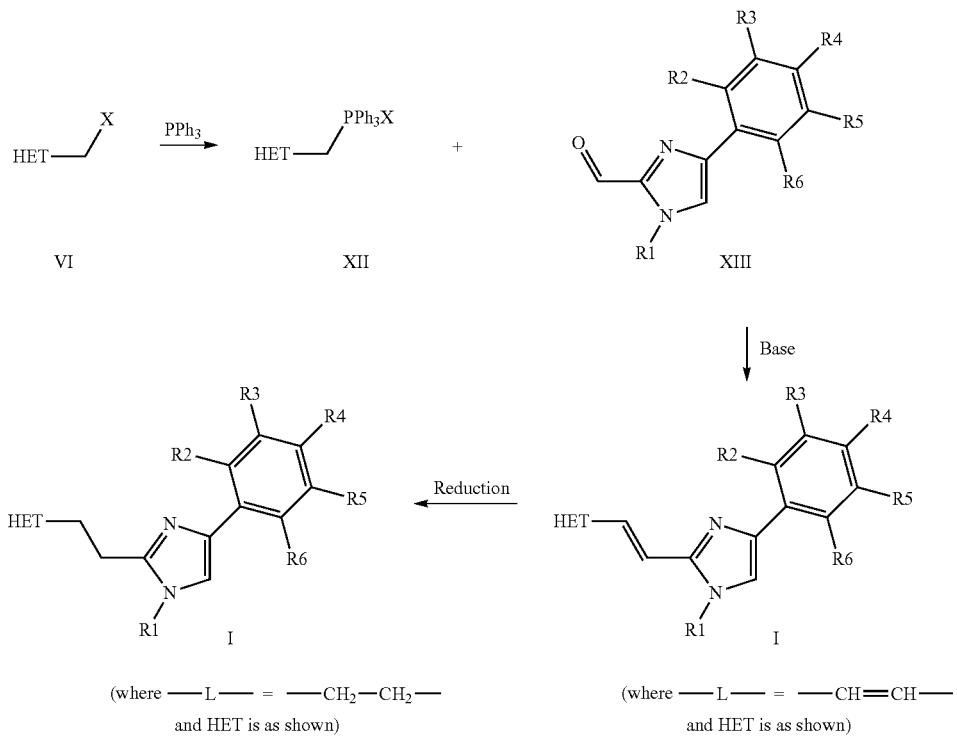

Specifically, compounds of formula I, wherein -L- is —CH$_2$—CH$_2$— can be prepared by reduction of an alkene of formula I, wherein -L- is —CH=CH—, by hydrogenation using a transition metal catalyst, such as palladium metal, together with a hydrogen source, such as hydrogen gas, ammonium hydrogen carbonate, or cyclohexadiene. Said alkenes of formula I, wherein -L- is —CH=CH— can be prepared by the Wittig reaction between a phosphonium salt of formula XII and an aldehyde of formula XIII in a suitable solvent, such as tetrahydrofuran, in the presence of a suitable base, such as 1,8-diazabicyclo[5.4.0]undec-7-ene. Phosphonium salt of formula XII are readily available by reaction of compounds of formula VI (see scheme 2 above) with triphenylphosphine by methods known to chemists skilled in the art. Aldehydes of formula XIII are readily available by oxidation of alcohols of formula V (see scheme 2 above) by methods known to chemists skilled in the art, e.g. by reacting alcohols of formula V with a suitable oxidizing agent, such as Dess-Martin periodinane, in a suitable solvent, such as dichloromethane or 1,2-dicholorethane.

The invention disclosed herein is further illustrated by the following non-limiting examples.

General Methods

Analytical LC-MS data were obtained using one of the following methods.

Method A:

A PE Sciex API 150EX instrument equipped with atmospheric pressure photo ionisation and a Shimadzu LC-8A/SLC-10A LC system was used. Column: 4.6×30 mm Waters Symmetry C18 column with 3.5 μm particle size; Column temperature: 60° C.; Solvent system: A=water/trifluoroacetic acid (100:0.05) and B=water/acetonitrile/trifluoroacetic acid (5:95:0.035); Method: Linear gradient elution with A:B=90:10 to 0:100 in 2.4 minutes and with a flow rate of 3.3 mL/min.

Method B:

An Agilent 1100 LCMS system with a G1946C or a G1946A mass detector was used. Column: 2.0×50 mm YMC ODS-AQ with 5 μm particle size; Column temperature: 50° C.; Solvent system: A=water/trifluoroacetic acid (99.9:0.1) and B=acetonitrile/trifluoroacetic acid (99.95:0.05); Method: Linear gradient elution with A:B=95:5 to 0:100 in 3.5 minutes and with a flow rate of 0.8 mL/min.

Method C:

A PE Sciex API 300 instrument equipped with atmospheric pressure photo ionisation and a Waters UPLC system was used. Column: Acquity UPLC BEH C$_{18}$ 1.7 μm, 2.1×50 mm (Waters); Column temperature: 60° C.; Solvent system: A=water/trifluoroacetic acid (100:0.05) and B=water/acetonitrile/trifluoroacetic acid (5:95:0.035); Method: Linear gradient elution with A:B=90:10 to 0:100 in 1.0 minutes and with a flow rate of 1.2 mL/min.

Method D:

An Agilent 1100 LCMS system with a G1946C or a G1946A mass detector was used. Column: 2.0×50 mm YMC ODS-AQ with 5 μm particle size; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 3.4 minutes and with a flow rate of 0.8 mL/min.

Method E:

A PE Sciex API 150EX instrument equipped with atmospheric pressure photo ionisation and a Shimadzu LC-8A/SLC-10A LC system was used. Column: 4.6×30 mm Waters Symmetry C18 column with 3.5 μm particle size; Column temperature: 60° C.; Solvent system: A=water/trifluoroacetic acid (99.95:0.05) and B=methanol/trifluoroacetic acid (99.965:0.035); Method: Linear gradient elution with A:B=83:17 to 0:100 in 2.4 minutes and with a flow rate of 3.0 mL/min.

Preparative LC-MS-purification was performed on a PE Sciex API 150EX instrument with atmospheric pressure chemical ionization. Column: 50×20 mm YMC ODS-A with 5 μm particle size; Method: Linear gradient elution with A:B=80:20 to 0:100 in 7 minutes and with a flow rate of 22.7 mL/minute. Fraction collection was performed by split-flow MS detection.

$^1$H NMR spectra were recorded at 500.13 MHz on a Bruker Avance AV500 instrument or at 250.13 MHz on a Bruker Avance DPX250 instrument. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, br s=broad singlet and br=broad signal.

Abbreviations are in accordance with to the ACS Style Guide: "The ACS Styleguide—A manual for authors and editors" Janet S. Dodd, Ed. 1997, ISBN: 0841234620

Preparation of Intermediates

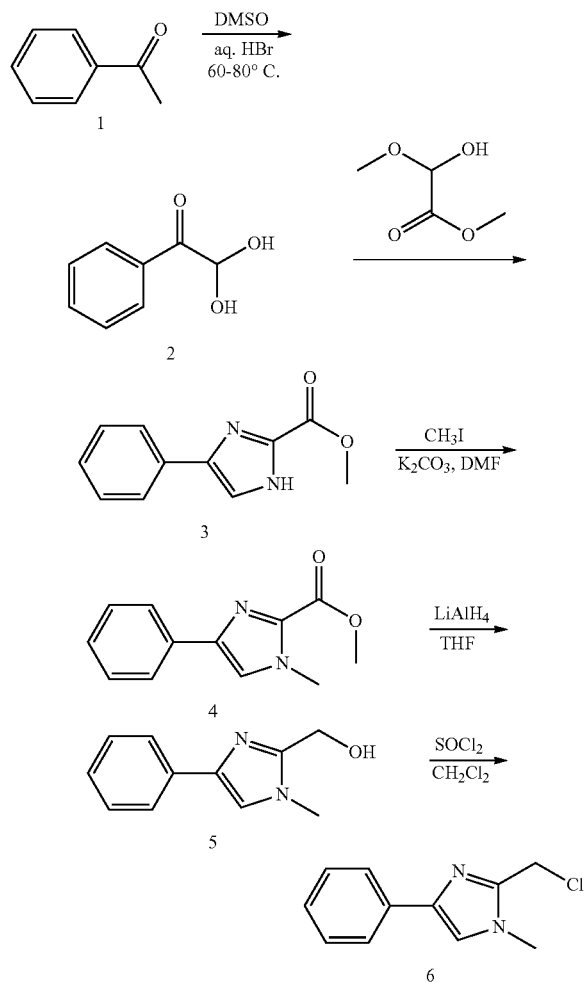

An adaptation of the method described by Song et al., *J. Org. Chem.* 1999, 64, 1859 was used. To a round-bottom flask equipped with a nitrogen inlet, a gas outlet to a bleach scrubber and a temperature probe was charged DMSO (113 mL) and acetophenone 1 (10 g, 83.2 mmol). The solution was heated to 60° C., and aqueous HBr was added slowly via an addition funnel while maintaining the reaction temperature between 60° C. and 68° C. A nitrogen sweep was employed to remove the dimethyl sulfide as it was formed. Once the HBr addition was complete, the internal temperature was maintained at 65° C. with external heating until the reaction was complete. The reaction was quenched by pouring the reaction mixture into water, extracted by ethyl acetate and afforded 2,2-dihydroxy-1-phenyl-ethanone 2. The reaction was monitored by TLC.

To a round-bottom flask charged with methyl 2-hydroxy-2-methoxyacetate (2.14 g, 25.9 mmol) and ammonium acetate (4.108 g, 52 mmol) in methanol (30 mL), acetic acid (30 mL) was added dropwise, followed by the addition of a solution of 2,2-dihydroxy-1-phenylethanone 2 (2 g, 13 mmol) in methanol with stirring. After 1.5 hours, the reaction mixture was concentrated in vacuo and was then mixed with 0.5 N hydrochloric acid. The solution was washed with ethyl acetate. The aqueous layer was basified with 5N sodium hydroxide to pH=9 and extracted with ethyl acetate 3 times. The combined organic layer was dried over Na$_2$SO$_4$. The solution was concentrated to dryness to give the compound 4-Phenyl-1H-imidazole-2-carboxylic acid methyl ester 3.

To a solution of compound 3 (1.0 g, 5 mmol) in DMF (20 mL) was added iodomethane (4 mL, 7.5 mmol) and K$_2$CO$_3$ (1.0 g, 7.5 mmol), and the mixture was stirred at 60° C. for 1 hour until TLC (petroleum ether/EtOAc=5/1) showed that compound 3 was consumed completely. The reaction mixture was diluted with brine (20 mL) and was extracted with ethyl acetate (2×10 mL). The combined organic layers were dried over anhydrous Na$_2$SO$_4$, filtered, and concentrated under vacuum to afford compound 4 (0.83 g, 78%). $^1$H NMR (400 MHz, CDCl$_3$): δ 7.81-7.78 (m, 2H), 7.39-7.35 (m, 2H), 7.32 (s, 1H), 7.29-7.25 (m, 1H), 4.05 (s, 3H), 3.97 (s, 3H).

To a solution of compound 4 (0.8 g, 3.7 mmol) in THF (8 mL) was added LiAlH$_4$ (0.21 g, 5.5 mmol) at −5° C. under N$_2$. The mixture was stirred at −10° C. for 2 hours and was quenched by aqueous NH$_4$Cl solution at 0° C. until pH reached 6. The resulting mixture was extracted with EtOAc (3×20 mL), and the combined organic layers were washed with brine (30 mL), dried over Na$_2$SO$_4$, filtered, and concentrated under reduced pressure to afford compound 5 (0.5 g, 75%). $^1$H NMR (400 MHz, DMSO-d$_6$): δ 7.69-7.67 (m, 2H), 7.53 (s, 1H), 7.30 (t, J=7.6 Hz, 2H), 7.15-7.12 (m, 1H), 5.30 (t, J=5.6 Hz, 1H), 4.48 (d, J=5.6 Hz, 2H), 3.65 (s, 3H).

To a solution of (1-Methyl-4-phenyl-1H-imidazol-2-yl)-methanol 5 (0.2 g, 0.097 mmol) was added SOCl$_2$ (0.14 g, 0.121 mmol), and the mixture was stirred at room temperature overnight. The mixture was evaporated to afford 2-Chloromethyl-1-methyl-4-phenyl-1H-imidazole 6, which was used without purification. $^1$H NMR (400 MHz, DMSO-d$_6$): δ8.24 (s, 1H), 7.87 (d, J=6.8 Hz, 2H), 7.54-7.49 (m, 2H), 7.43-7.41 (m, 1H), 5.24 (s, 2H), 3.89 (s, 3H).

The following intermediates were prepared in a similar way:

2-Chloromethyl-1-ethyl-4-phenyl-1H-imidazole

95% yield, $^1$H NMR (400 MHz, DMSO-d$_6$): δ 8.36 (s, 1H), 7.92-7.89 (m, 2H), 7.51-7.47 (m, 2H), 7.43-7.39 (m, 1H), 5.26 (s, 2H), 4.24 (q, J=7.2 Hz, 2H), 1.46 (t, J=7.2 Hz, 3H).

2-Chloromethyl-1-isopropyl-4-phenyl-1H-imidazole

100% yield, $^1$H NMR (400 MHz, DMSO-d$_6$): δ 8.54 (s, 1H), 7.93 (d, J=7.6 Hz, 2H), 7.52-7.29 (m, 3H), 5.28 (s, 2H), 4.84-4.75 (m, 1H), 1.50 (d, J=6.8 Hz, 6H).

2-chloromethyl-4-(2-fluorophenyl)-1-methyl-1H-imidazole

80% yield, $^1$H NMR (400 MHz, DMSO-d$_6$): δ 8.06-8.02 (m, 1H), 7.91 (d, J=3.2 Hz, 1H), 7.41-7.38 (m, 1H), 7.34-7.29 (m, 2H), 5.12 (s, 2H), 3.84 (s, 3H).

2-chloromethyl-4-(3-fluorophenyl)-1-methyl-1H-imidazole

89% yield, ¹H NMR (400 MHz, Methanol-d₄): δ 8.07 (s, 1H), 7.58-7.51 (m, 3H), 7.27-7.23 (m, 1H), 5.11 (s, 2H), 4.01 (s, 3H).

2-chloromethyl-4-(4-fluorophenyl)-1-methyl-1H-imidazole

74% yield, ¹H NMR (400 MHz, DMSO-d₅): δ 8.19 (s, 1H), 7.94-7.91 (m, 2H), 7.37-7.33 (m, 2H), 5.20 (s, 2H), 3.86 (s, 3H).

2-chloromethyl-4-(2-chlorophenyl)-1-methyl-1H-imidazole

74% yield, ¹H NMR (400 MHz, DMSO-d₆): δ 8.11 (s, 1H), 7.89 (dd, J=7.6 Hz, 1.6 Hz, 1H), 7.59 (d, J=7.6 Hz, 1H), 7.48-7.38 (m, 2H), 5.13 (s, 2H), 3.87 (s, 3H).

2-chloromethyl-4-(3-chlorophenyl)-1-methyl-1H-imidazole

99% yield, ¹H NMR (400 MHz, DMSO-d₆): δ 8.30 (s, 1H), 8.00-7.99 (m, 1H), 7.84 (m, 1H), 7.52-7.43 (m, 2H), 5.20 (s, 2H), 3.86 (s, 3H).

2-chloromethyl-4-(4-chlorophenyl)-1-methyl-1H-imidazole

80% yield, ¹H NMR (400 MHz, Methanol-d₄): δ 8.00 (s, 1H), 7.71 (d, J=8.4 Hz, 2H), 7.56 (d, J=8.4 Hz, 2H), 5.10 (s, 2H), 4.01 (s, 3H).

2-chloromethyl-4-(2-methoxyphenyl)-1-methyl-1H-imidazole

93% yield, ¹H NMR (400 MHz, DMSO-d₆): δ 8.12 (s, 1H), 7.98 (dd, J=8.0 Hz, 1.6 Hz, 1H), 7.45-7.40 (m, 1H), 7.20 (d, J=8.0 Hz, 1H), 7.13-7.06 (m, 1H), 5.27 (s, 2H), 3.93 (s, 3H), 3.90 (s, 3H).

2-chloromethyl-4-(3-methoxyphenyl)-1-methyl-1H-imidazole

90% yield, ¹H NMR (300 MHz, Methanol-d₄): δ8.05 (s, 1H), 7.55-7.44 (m, 1H), 7.32-7.24 (m, 2H), 7.14-7.06 (m, 1H), 5.12 (s, 2H), 4.03 (s, 3H), 3.90 (s, 3H).

2-chloromethyl-4-(4-methoxyphenyl)-1-methyl-1H-imidazole

97% yield, ¹H NMR (400 MHz, DMSO-d₆): δ 8.10 (s, 1H), 7.79 (d, J=8.8 Hz, 2H), 7.02 (d, J=8.8 Hz, 2H), 5.20 (s, 2H), 3.83 (s, 3H), 3.75 (s, 3H).

2-Chloromethyl-4-phenyl-1H-imidazole (by omission of the methylation step)

81% yield, ¹H NMR (400 MHz, DMSO-d₆): δ8.21 (s, 1H), 7.96-7.92 (m, 2H), 7.59-7.55 (m, 2H), 7.50-7.47 (m, 1H), 5.12 (s, 2H).

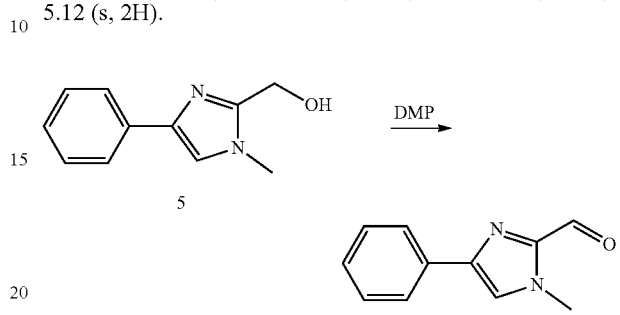

To a solution of (1-Methyl-4-phenyl-1H-imidazol-2-yl)-methanol 5 (50.0 mg, 0.266 mmol) in 1,2-dichloroethane (4.0 mL) under Ar was added Dess-Martin periodinane (124 mg, 0.292 mmol), and the mixture was stirred at room temperature for 2 hours. Saturated NaHCO₃ solution was added, the organic layer was separated and the aqueous layer was extracted with 1,2-dichloroethane. The combined organic layers were dried over Na₂SO₄, volatiles were evaporated and the residue was purified by silica gel chromatography on a FlashMaster system (gradient elution; 0-100% ethylacetate in heptane) to afford the title compound as a white solid (39.1 mg, 79%). ¹H NMR (500 MHz, DMSO-d₆): δ9.76 (s, 1H), 8.11 (s, 1H), 7.84 (d, J=7.7 Hz, 2H), 7.42 (t, J=7.6 Hz, 2H), 7.30 (t, J=7.4 Hz, 1H), 3.99 (s, 3H).

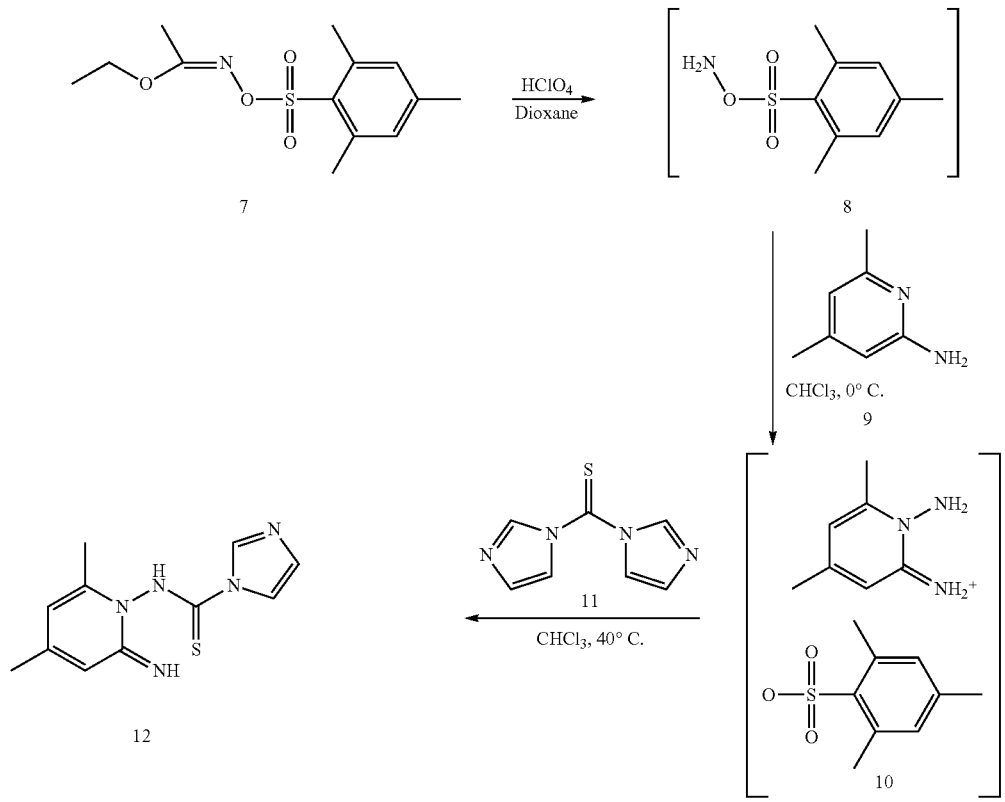

An adaptation of the method described in WO 96/01826 was used. To a solution of ethyl O-mesitylsulfonylacetohydroxamate 7 (1.7 g, 6.0 mmol) in 1,4-dioxane (10 mL) cooled in an ice bath (freezes at 8-9° C.) was added 70% perchloric acid (7.5 mL) dropwise over 15 minutes, maintaining internal temperature below 15° C. The mixture was then diluted with ice water (100 mL) to precipitate the product O-(mesitylsulfonyl)hydroxylamine 8 which was filtered off, washed thoroughly with water, and immediately dissolved in chloroform (10 mL) while still wet (CAUTION! 8 is explosive when dry!). The organic layer was separated and was passed through a plug of $Na_2SO_4$ in a fritted syringe to remove water. The so obtained solution of O-(mesitylsulfonyl)hydroxylamine 8 was added dropwise to a solution of 2-amino-4,6-dimethylpyridine 9 (0.611 g, 5.00 mmol) in chloroform (10 mL) cooled in an ice bath. The mixture was then warmed to room temperature and was stirred for 2 hours to effect conversion to intermediate 10. Into the reaction mixture was then added 1,1'-thiocarbonyldiimidazole 11 (1.16 g, 6.5 mmol) and the resulting mixture was stirred at 40° C. overnight. Volatiles were evaporated and the residue was chromatographed on silica gel (gradient elution with heptane:ethyl acetate 100:0→0:100) to yield imidazole-1-carbothioic acid (2-imino-4,6-dimethyl-2H-pyridin-1-yl)-amide 12 as an off-white solid (0.50 g, 40%) containing a minor amount of residual imidazole. $^1$H NMR (500 MHz, DMSO-$d_6$): δ7.88 (s, 1H), 7.64 (s, 1H), 7.42 (br s, 2H), 6.93 (s, 1H), 6.69 (s, 1H), 6.67 (s, 1H), 2.28 (s, 3H), 2.27 (s, 3H).

The following intermediates were prepared analogously, except that they were used for the preparation of final compounds without prior purification or characterization:
Imidazole-1-carbothioic acid (5-bromo-2-imino-4-methyl-2H-pyridin-1-yl)-amide
Imidazole-1-carbothioic acid (5-bromo-2-imino-4,6-dimethyl-2H-pyridin-1-yl)-amide
Imidazole-1-carbothioic acid (5-chloro-2-imino-3-methyl-2H-pyridin-1-yl)-amide
Imidazole-1-carbothioic acid (5-cyano-2-imino-2H-pyridin-1-yl)-amide The following intermediate was prepared analogously:
4-Phenyl-1,3-dihydro-imidazole-2-thione
80% yield, $^1$H NMR (500 MHz, DMSO-$d_6$): δ 12.53 (br s, 1H), 12.15 (br s, 1H), 7.69-7.65 (m, 2H), 7.41-7.35 (m, 3H) 7.27 (t, J=7.4 Hz, 1H).

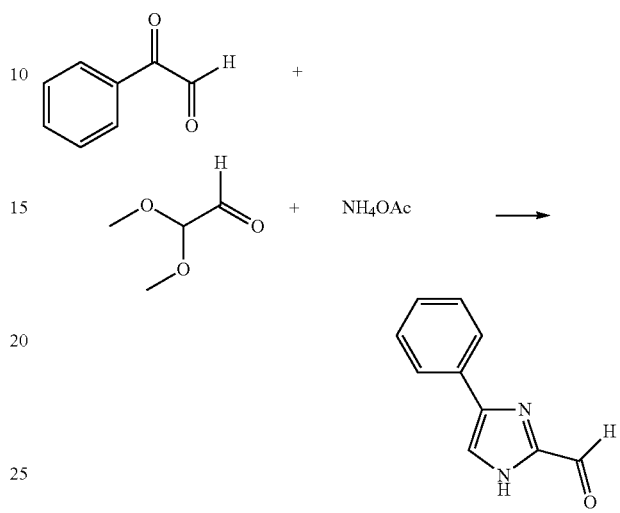

A solution of phenylglyoxal monohydrate (102 g, 0.67 mol) and glyoxal dimethyl acetal (60% solution in water, 232 mL, 1.54 mol) in methanol (1.1 L) was treated with a solution of ammonium acetate 8202 g, 2.61 mol) in methanol (1.1 L) and the resulting solution stirred at RT for 16 h. The volatiles were removed in vacuo and the residue slurried in 2N HCl solution (1.1 L) and heated at 80° C. for 30 min. The cooled solution was extracted with EtOAc (200 mL) and the separated aqueous layer was basified to pH 9 with 9N NaOH solution. The solids were filtered, washed with water and dried in vacuo to yield the title compound (97.2 g, 84%) as a light brown solid. LC-MS: m/z=173.0 (MH$^+$), $t_R$=0.66 min, method C

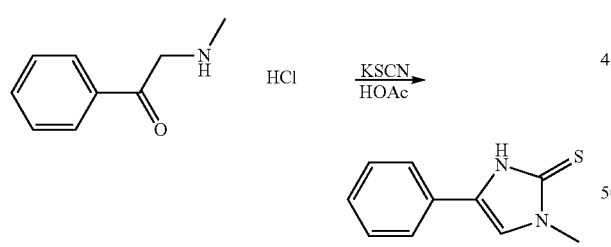

An adaptation of the method reported by Kjellin and Sandström, Acta Chem. Scand. 1969, 23, 2879-2887 was used. A mixture of 2-methylamino-1-phenyl-ethanone hydrochloride (0.754 g, 4.06 mmol) (see e.g. Hyde et al. J. Am. Chem. Soc. 1928, 50, 2287-2292; Shang et al. Chem. Eur. J. 2007, 13, 7780-7784) and potassium thiocyanate (0.434 g, 4.46 mmol) in acetic acid (12 mL) was heated at 140° C. for 10 minutes using a microwave synthesizer. Dilution with water (50 mL) and cooling in an ice bath caused the product to precipitate. It was collected by filtration, washed with water, and vacuum dried to yield the title compound (0.365 g, 47%) pure as an off-white solid. $^1$H NMR (500 MHz, DMSO-$d_6$): δ12.66 (br s, 1H), 7.65 (d, J=7.6 Hz, 2H), 7.60 (s, 1H), 7.39 (l, J=7.8 Hz, 2H), 7.27 (t, J=7.4 Hz, 1H), 3.49 (s, 3H).

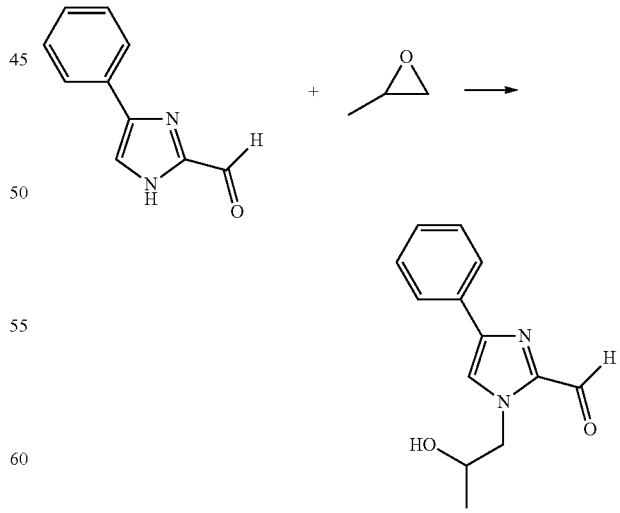

In a closed vessel a slurry of 4-phenyl-1H-imidazole-2-carbaldehyde (200 mg, 1.16 mmol) and sodium carbonate (60 mg, 0.6 mmol) in ethanol (4 mL) was treated with propylene oxide (170 µL, 2.4 mmol) and heated at 100° C. for 3 h. The cooled solution was filtered and the solids washed with DCM. The volatiles were removed in vacuo to yield the crude title compound which was used without further purification (250 mg, 63%). LC-MS: m/z=231.5 (MH$^+$), t$_R$=0.41 min, method A The following intermediates were prepared analogously, except that they were used for the preparation of final compounds without prior purification or characterization:

(S)-1-(2-Hydroxypropyl)-4-Phenyl-1H-imidazole-2-carbaldehyde (R)-1-(2-Hydroxypropyl)-4-Phenyl-1H-imidazole-2-carbaldehyde 1-(2-Hydroxy-2-methyl-propyl)-4-phenyl-1H-imidazole-2-carbaldehyde from 1-chloro-2-methyl-2-propanol.

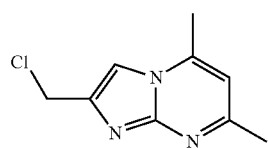

A solution of 2-amino-4,6-dimethylpyrimidine (2.46 g, 20.0 mmol) and 1,3-dichloro-2-propanone (2.67 g, 21.0 mmol) in 1,2-dimethoxyethane (20 mL) was stirred at 45° C. overnight. A precipitate formed, and this was collected by filtration, and was then refluxed with ethanol (15 mL) for 2 hours. After cooling to room temperature, the product precipitated as white needles which were collected by filtration and vacuum dried to yield the title compound pure as its hydrochloride salt (883 mg, 19%). $^1$H NMR (500 MHz, DMSO-d$_6$): δ 7.84 (s, 1H), 6.88 (s, 1H), 4.84 (s, 2H), 2.60 (s, 3H), 2.49 (s, 3H).

The following intermediate was prepared analogously, but with a 90° C. reaction temperature for the first step:

2-Chloromethyl-imidazo[1,2-a]pyrimidine hydrochloride

62% yield, LC-MS: m/z=168.2 (MH$^+$), t$_R$=0.13 min, method A.

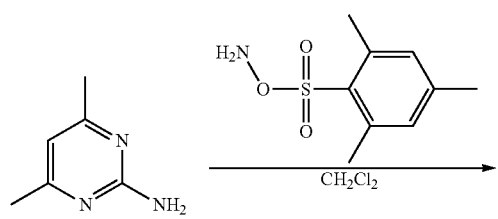

4,6-Dimethyl-pyrimidin-2-ylamine

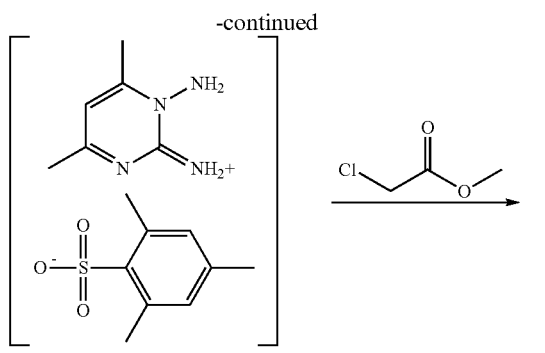

1-Amino-4,6-dimethyl-1H-pyrimidin-2-ylidene-ammonium 2,4,6-Trimethyl-benzenesulfonate

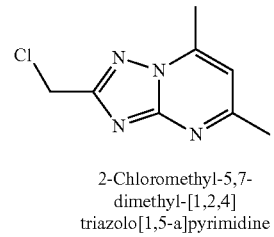

2-Chloromethyl-5,7-dimethyl-[1,2,4]triazolo[1,5-a]pyrimidine

To a solution of 4,6-Dimethyl-pyrimidin-2-ylamine (25 g, 200 mmol) in 400 mL of CH$_2$Cl$_2$ was added dropwise a solution of hydroxylamine-2,4,6-Trimethyl-benzenesulfonate (105 g, 488 mmol) in 300 mL of CH$_2$Cl$_2$ at 0° C., and the mixture was stirred at 0° C. for 1 h and filtered. The solid collected was washed with CH$_2$Cl$_2$ (100 mL) to give 1-Amino-4,6-dimethyl-1H-pyrimidin-2-ylidene-ammonium 2,4,6-Trimethyl-benzenesulfonate (40 g, yield: 62%).

A mixture of 1-Amino-4,6-dimethyl-1H-pyrimidin-2-ylidene-ammonium 2,4,6-Trimethyl-benzenesulfonate (40 g, 0.1 mol) and NaOH (10 g, 0.2 mol) in 500 mL of EtOH was stirred at 50-60° C. for 1 hour. After chloroacetic acid methyl ester (16.6 g, 0.15 mol) was added, the resultant mixture was stirred at reflux for 4 hours. After being concentrated under reduce pressure, the residue was diluted with water (1000 mL) and extracted with CH$_2$Cl$_2$ (300 mL×3). The combined organic layers were washed with brine (200 mL), dried over Na$_2$SO$_4$, filtered, and concentrated under vacuum. The residue was purified by column chromatography on silica gel (petroleum ether/EtOAc=2/1) to give 2 g of 2-Chloromethyl-5,7-dimethyl-[1,2,4]triazolo[1,5-a]pyrimidine in 9% yield. $^1$H NMR (300 MHz, DMSO-d$_6$): δ8.55 (s, 1H), 6.25 (s, 2H), 4.05 (s, 3H), 3.95 (s, 3H); LC-MS (MH$^+$): m/z=196.9, t$_R$ (min, method A)=0.52

The following intermediates were prepared analogously:

7-Chloro-2-chloromethyl-5,8-dimethyl-[1,2,4]triazolo[1,5-c]pyrimidine from 6-Chloro-2,5-dimethyl-pyrimidine-4-ylamine prepared as described by Henze et al. J. Org. Chem 1952, 17, 1320-1327. 3.2% yield, LC-MS: m/z=231.5 (MH$^+$), t$_R$=1.13 min, method E 2-Chloromethyl-5,8-dimethyl-[1,2,4]-triazolo[1,5-a]pyrazine from 2-amino-3,6-dimethylpyrazine. 60% yield, $^1$H NMR (500 MHz, CDCl$_3$): δ7.91 (s, 1H), 4.87 (s, 2H), 2.91 (s, 3H), 2.74 (s, 3H), LC-MS: m/z=196.9 (MH$^+$), t$_R$=0.64 min, method A 2-Chloromethyl-5,8-dimethyl-[1,2,4]triazolo[1,5-a]pyridine from 6-Chloro-5-ethyl-2-methyl-pyrimidin-4-ylamine. 21% yield, LC-MS: m/z=245.0 (MH$^+$), t$_R$=0.72 min, method A

2-Chloromethyl-8-methoxy-5-methyl-[1,2,4]triazolo[1,5-a] pyridine from 3-Methoxy-6-methyl-pyridin-2-ylamine

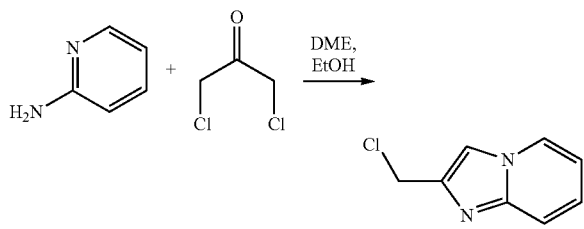

The method of Vanelle et al. *Tetrahedron* 1991, 47, 5173-5184 was used. To a solution of 1,3-dichloro-2-propanone (2.69 g, 21.2 mmol) in 1,2-dimethoxyethane (5 mL) was added 2-aminopyridine and the mixture was stirred at room temperature for 2 hours. During this time a thick precipitate formed, and this was collected by filtration. The precipitate was refluxed in absolute ethanol for 2 hours after which volatiles were removed by evaporation. The residue was dissolved in water (30 mL) and solid NaHCO$_3$ was added to neutralize the mixture. A white precipitate formed, and this was collected by filtration, washed with water and vacuum dried to yield the title compound pure as a cream white solid (1.43 g, 42%). $^1$H NMR (500 MHz, CDCl$_3$): δ8.08 (d, J=6.7 Hz, 1H), 7.62 (s, 1H), 7.58 (d, J=9.0 Hz, 1H), 7.17-7.22 (m, 1H), 6.80 (t, J=6.8 Hz, 1H), 4.78 (s, 2H).

The following intermediate was prepared analogously:
2-Chloromethyl-8-methyl-imidazo[1,2-a]pyridine 53% yield, $^1$H NMR (500 MHz, CDCl$_3$): δ 7.95 (d, J=6.9 Hz, 1H), 7.61 (s, 1H), 6.97 (dt, J=7.0 Hz, 1.1 Hz, 1H), 6.70 (t, J=6.8 Hz, 1H), 4.80 (s, 2H), 2.60 (s, 3H).

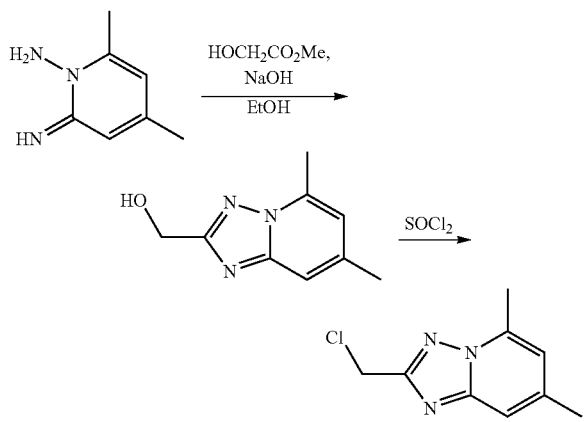

To a solution of 0.79 g of sodium hydroxide in ethanol (20 mL) was added 2-imino-4,6-dimethyl-2H-pyridin-1-ylamine (1.7 g, 0.012 mol; obtained by HPLC purification of intermediate 10). After being stirred at 50-60° C. for 1 hour, methyl glycolate (1.4 g, 0.016 mop was added, and the resulting mixture was stirred at reflux for 6 hours. After removal of the solvent under reduced pressure, the residue was purified by column chromatography on silica gel (ethyl acetate) to afford (5,7-Dimethyl-[1,2,4]triazolo[1,5-a]pyridin-2-yl)-methanol (0.2 g, 10%); $^1$H NMR (300 MHz, DMSO-d$_6$): δ 7.39 (s, 1H), 6.87 (s, 1H), 5.38 (t, J=6.3 Hz, 1H), 4.59 (d, J=6.3 Hz, 2H), 2.64 (s, 3H), 2.38 (s, 3H). A mixture of this compound (31 mg, 0.175 mmol) and SOCl$_2$ (10 mL) in dry CH$_2$Cl$_2$ (10 mL) was stirred at room temperature for 2 hours. The solvent and excess SOCl$_2$ was evaporated under vacuum to yield the title compound as a crude product, which was used for the preparation of final compounds without purification or characterization.

The following compounds are known in the art:
2-Chloromethyl-1-phenyl-1H-benzoimidazole (JP 59176277).
1-Methyl-1,3-dihydro-benzoimidazole-2-thione (Wilde et al. *Bioorg. Med. Chem. Lett.* 1995, 5, 167-172).
1-Phenyl-1,3-dihydro-benzoimidazole-2-thione (Kidwal et al. *J. Korean Chem. Soc.* 2005, 49, 288-291).
[1,2,4]Triazolo[1,5-a]pyrimidine-2-thione (Brown et al. *Aust. J. Chem.* 1978, 31, 397-404).
1,3-Dihydro-imidazo[4,5-b]pyridine-2-thione (Yutilov et al. *Khim. Geter. Soedin.* 1988, 799-804).
Pyrazolo[1,5-a]pyridin-2-yl-methanol (Tsuchiya, T.; Sashida, H. *J. Chem. Soc., Chem. Commun.* 1980, 1109-1110; Tsuchiya, T.; Sashida, H; Konoshita, A. *Chem. Pharm. Bull.* 1983, 31, 4568-4572).

Preparation of the Compounds of the Invention

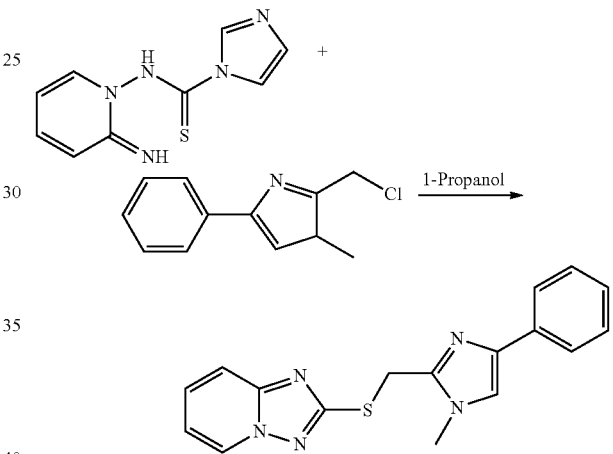

An adaptation of the method described in WO 96/01826 was used. Imidazole-1-carbothioic acid (2-imino-2H-pyridin-1-yl)-amide (200 mg, 1.37 mmol) and 2-chloromethyl-1-methyl-4-phenyl-1H-imidazole 6 (300 mg, 1.46 mmol) were dissolved in 1-propanol (25 mL) and the mixture was heated to reflux for 2 hours. The solvent was removed under reduced pressure and the residue dissolved in dichloromethane. The solution was washed with water and the organic layer was dried over Na$_2$SO$_4$ and concentrated. The residue was purified by chromatography on silica gel to afford the title compound (273 mg, 62%) as a yellow solid. LC-MS: m/z=322.1 (MH$^+$), t$_R$=2.29 min, method B.

The following compounds of the invention were prepared analogously:

7-Methyl-2-(1-methyl-4-phenyl-1H-imidazol-2-ylmethylsulfanyl)-[1,2,4]triazolo[1,5-a]pyridine (from imidazole-1-carbothioic acid (2-imino-4-methyl-2H-pyridin-1-yl)-amide (see WO 96/01826) and 2-chloromethyl-1-methyl-4-phenyl-1H-imidazole 6). LC-MS: m/z=336.5 (MH$^+$), t$_R$=0.71 min, method A.

5,7-Dimethyl-2-(1-methyl-4-phenyl-1H-imidazol-2-ylmethylsulfanyl)-[1,2,4]triazolo[1,5-a]pyridine (from imidazole-1-carbothioic acid (2-imino-4,6-dimethyl-2H-pyridin-1-yl)-amide 12 and 2-chloromethyl-1-methyl-4-phenyl-1H-imidazole 6). LC-MS: m/z=350.3 (MH$^+$), t$_R$=0.79 min, method A.

2-(1-Methyl-4-phenyl-1H-imidazol-2-ylmethylsulfanyl)[1,2,4]triazolo[1,5-a]pyrimidine (from [1,2,4]triazolo[1,5-a]pyrimidine-2-thiol (commercially available; see also Brown of al. *Aust. J. Chem.* 1978, 31, 397-404) and 2-chloromethyl-1-methyl-4-phenyl-1H-imidazole 6). LC-MS: m/z=323.1 (MH$^+$), t$_R$=2.07 min, method B.

2-(1-Methyl-4-phenyl-1H-imidazol-2-ylmethylsulfanyl)-1H-imidazo[4,5-b]pyridine (from 1,3-dihydro-2H-Imidazo[4,5-b]pyridine-2-thione (commercially available; see also Yutilov et al. *Khim. Geter. Soedin.* 1 988, 799-804) and 2-chloromethyl-1-methyl-4-phenyl-1H-imidazole 6). LC-MS: m/z=322.1 (MH$^+$), t$_R$=2.01 min, method B.

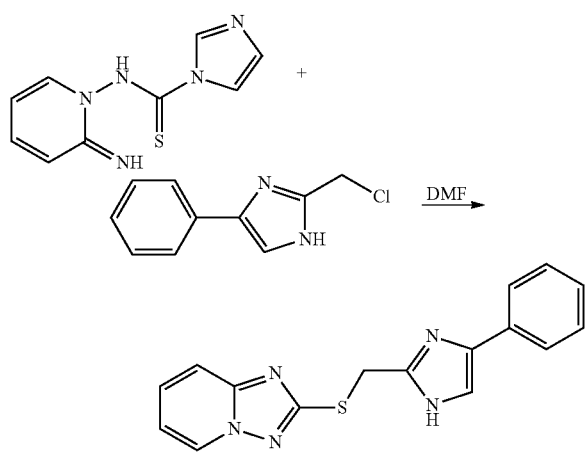

A solution of imidazole-1-carbothioic acid (2-imino-2H-pyridin-1-yl)-amide (18 mg, 0.080 mmol) in DMF (0.5 mL) was added to 2-chloromethyl-5-phenyl-1H-imidazole (23 mg, 0.12 mmol) and the mixture was heated at 100° C. overnight. Volatiles were evaporated and the residue was purified by preparative LC-MS to yield the title compound. LC-MS: m/z=308.2 (MH$^+$), t$_R$=0.67 min, method A.

The following compounds of the invention were prepared analogously:

2-[4-(3-Chloro-phenyl)-1-methyl-1H-imidazol-2-ylmethylsulfanyl]-[1,2,4]triazolo[1,5-a]pyridine. LC-MS: m/z=356.4 (MH$_+$), t$_R$=0.76 min, method A.

2-(1-Ethyl-4-phenyl-1H-imidazol-2-ylmethylsulfanyl)-[1,2,4]triazolo[1,5-a]pyridine. LC-MS: m/z=336.4 (MH$^+$), t$_R$=0.69 min, method A.

2-(1-Isopropyl-4-phenyl-1H-imidazol-2-ylmethylsulfanyl)-[1,2,4]-triazolo[1,5-a]pyridine. LC-MS: m/z=350.3 (MH$^+$), t$_R$=0.77 min, method A.

2-[4-(4-Fluoro-phenyl)-1-methyl-1H-imidazol-2-ylmethylsulfanyl]-5,7-dimethyl-[1,2,4]triazolo[1,5-a]pyridine. LC-MS: m/z=368.2 (MH$^+$), t$_R$=0.83 min, method A.

2-[4-(3-Fluoro-phenyl)-1-methyl-1H-imidazol-2-ylmethylsulfanyl]-5,7-dimethyl-[1,2,4]triazolo[1,5-a]pyridine. LC-MS: m/z=368.3 (MH$^+$), t$_R$=0.84 min, method A.

2-[4-(3-Chloro-phenyl)-1-methyl-1H-imidazol-2-ylmethylsulfanyl]-5,7-dimethyl-[1,2,4]triazolo[1,5-a]pyridine. LC-MS: m/z=384.3 (MH$^+$), t$_R$=0.93 min, method A.

2-(1-Ethyl-4-phenyl-1H-imidazol-2-ylmethylsulfanyl)-5,7-dimethyl-[1,2,4]triazolo[1,5-a]pyridine. LC-MS: m/z=364.4 (MH$^+$), t$_R$=0.88 min, method A.

5,7-Dimethyl-2-(4-phenyl-1H-imidazol-2-ylmethylsulfanyl)-[1,2,4]triazolo[1,5-a]pyridine. LC-MS: m/z=336.4 (MH$^+$), t$_R$=0.78 min, method A.

2-[4-(4-Fluoro-phenyl)-1-methyl-1H-imidazol-2-ylmethylsulfanyl]-[1,2,4]triazolo[1,5-a]pyridine. LC-MS: m/z=340.3 (MH$^+$), t$_R$=0.65 min, method A.

2-[4-(3-Fluoro-phenyl)-1-methyl-1H-imidazol-2-ylmethylsulfanyl]-[1,2,4]triazolo[1,5-a]pyridine. LC-MS: m/z=340.3 (MH$^+$), t$_R$=0.65 min, method A.

2-[4-(4-Chloro-phenyl)-1-methyl-1H-imidazol-2-ylmethylsulfanyl]-5,7-dimethyl-[1,2,4]triazolo[1,5-a]pyridine. LC-MS: m/z=384.4 (MH$^+$), t$_R$=0.94 min, method A.

6-Bromo-7-methyl-2-(1-methyl-4-phenyl-1H-imidazol-2-ylmethylsulfanyl)[1,2,4]-triazolo[1,5-a]pyridine. LC-MS: m/z=414.1 (MH$^+$), t$_R$=0.89 min, method A.

6-Bromo-5,7-dimethyl-2-(1-methyl-4-phenyl-1H-imidazol-2-ylmethylsulfanyl)[1,2,4]-triazolo[1,5-a]pyridine. LC-MS: m/z=428.0 (MH$^+$), t$_R$=1.00 min, method A.

6-Chloro-8-methyl-2-(1-methyl-4-phenyl-1H-imidazol-2-ylmethylsulfanyl)-[1,2,4]triazolo[1,5-a]pyridine. LC-MS: m/z=370.1 (MH$^+$), t$_R$=0.87 min, method A.

2-(1-Methyl-4-phenyl-1H-imidazol-2-ylmethylsulfanyl)-[1,2,4]triazolo[1,5-a]pyridine-6-carbonitrile. LC-MS: m/z=347.0 (MH$^+$), t$_R$=0.64 min, method A.

2-[4-(2-Chloro-phenyl)-1-methyl-1H-imidazol-2-ylmethylsulfanyl]-5,7-dimethyl-[1,2,4]triazolo[1,5-a]pyridine. LC-MS: m/z=384.3 (MH$^+$), t$_R$=0.87 min, method A.

2-[4-(2-Fluoro-phenyl)-1-methyl-1H-imidazol-2-ylmethylsulfanyl]-5,7-dimethyl-[1,2,4]triazolo[1,5-a]pyridine. LC-MS: m/z=368.4 (MH$^+$), t$_R$=0.83 min, method A.

2-[4-(4-Methoxy-phenyl)-1-methyl-1H-imidazol-2-ylmethylsulfanyl]-5,7-dimethyl-[1,2,4]triazolo[1,5-a]pyridine. LC-MS: m/z=380.6 (MH$^+$), t$_R$=0.84 min, method A.

2-[4-(3-Methoxy-phenyl)-1-methyl-1H-imidazol-2-ylmethylsulfanyl]-5,7-dimethyl-[1,2,4]triazolo[1,5-a]pyridine. LC-MS: m/z=380.4 (MH$^+$), t$_R$=0.85 min, method A.

2-[4-(2-Methoxy-phenyl)-1-methyl-1H-imidazol-2-ylmethylsulfanyl]-5,7-dimethyl-[1,2,4]triazolo[1,5-a]pyridine. LC-MS: m/z=380.5 (MH$^+$), t$_{it}$=0.86 min, method A.

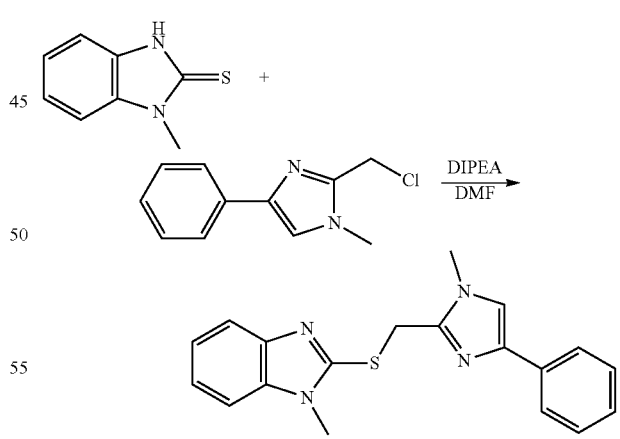

To a solution of 1-methyl-1,3-dihydro-benzoimidazole-2-thione (28 mg, 0.18 mmol) in DMF (1.6 mL) was added DIPEA (80 μL, 0.44 mmol) and 2-chloromethyl-1-methyl-4-phenyl-1H-imidazole (40 mg, 0.19 mmol). The mixture was heated at 90° C. for 10 minutes using a microwave synthesizer. Volatiles were evaporated and the residue was purified by preparative LC-MS to yield the title compound. LC-MS: m/z=335.3 (MH$^+$), t$_R$=0.51 min, method C.

The following compound of the invention was prepared analogously:
2-(1-Methyl-4-phenyl-1H-imidazol-2-ylmethylsulfanyl)-1-phenyl-1H-benzoimidazole. LC-MS: m/z=396.9 (MH$^+$), $t_R$=0.65 min, method C.
2-[4-(3-Methoxy-phenyl)-1-methyl-1H-imidazol-2-ylmethylsulfanyl]-5,7-dimethyl-[1,2,4]triazolo[1,5-a]pyrimidine, LC-MS (MH$^+$): m/z=381.5, $t_R$ (min, method A)=0.68
5,7-Dimethyl-2-(1-methyl-4-phenyl-1H-imidazol-2-ylmethylsulfanyl)-[1,2,4]triazolo[1,5-a]pyrimidine, LC-MS (MH$^+$): m/z=351.4, $t_R$ (min, method A)=0.62

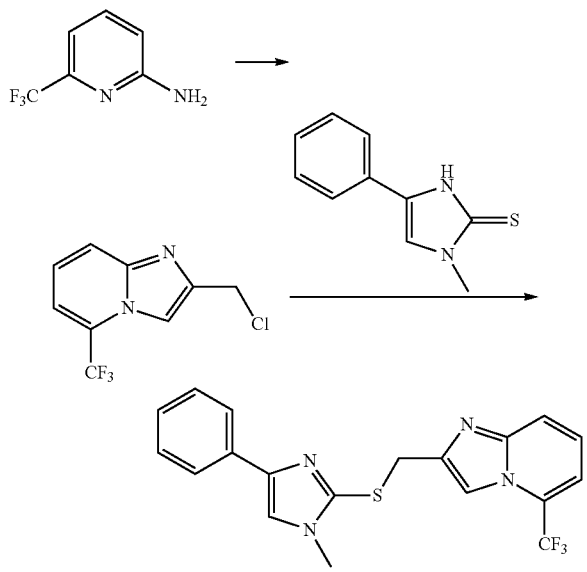

1,3-dichloroacetone (0.01 mL, 0.11 mmol) was added dropwise to a solution of 6-trifluoromethyl-pyridin-2-ylamine (0.016 g, 0.10 mmol) in 1,2-dimethoxyethane (1.0 mL), and the mixture was left to stir at room temperature for 2 h. The solvent was removed in vacuo and the resulting residue re-dissolved in ethanol (1.0 mL). The reaction mixture was subsequently heated under reflux for 2 h, and the solvent was removed under reduced pressure. DIPEA (0.05 mL, 0.25 mmol) and 1-methyl-4 phenyl-1,3-dihydro-imidazole-2-thione (0.017 g, 0.09 mmol) were sequentially added to a solution of the crude product in DMF (1.0 mL). The reaction mixture was then heated at 60° C. for 2 h after which LC-MS showed complete consumption of the starting materials. The solvent was removed under reduced pressure and the crude product purified using preparative LC-MS to yield the title compound. LC-MS: m/z=389.1 (MH$^+$), $t_R$=0.52 min, method C.

The following compounds of the invention were prepared analogously:
5-Methyl-2-(1-methyl-4-phenyl-1H-imidazol-2-ylsulfanylmethyl)-imidazo[1,2-a]pyridine. LC-MS: m/z=335.4 (MH$^+$), $t_R$=0.54 min, method A.
5,7-Dimethyl-2-(1-methyl-4-phenyl-1H-imidazol-2-ylsulfanylmethyl)-imidazo[1,2-a]pyridine. LC-MS: m/z=349.1 (MH$^+$), $t_R$=0.61 min, method A.
5-Chloro-2-(1-methyl-4-phenyl-1H-imidazol-2-ylsulfanylmethyl)-imidazo[1,2-a]pyridine. LC-MS: m/z=355.4 (MH$^+$), $t_R$=0.69 min, method A.
6-Chloro-8-methyl-2-(1-methyl-4-phenyl-1H-imidazol-2-ylsulfanylmethyl)-imidazo[1,2-a]pyridine. LC-MS: m/z=369.2 (MH$^+$), $t_R$=0.76 min, method A.

2-(1-Methyl-4-phenyl-1H-imidazol-2-ylsulfanylmethyl)-imidazo[1,2-a]pyridine-7-carbonitrile. LC-MS: m/z=346.2 (MH$^+$), $t_R$=0.66 min, method A.

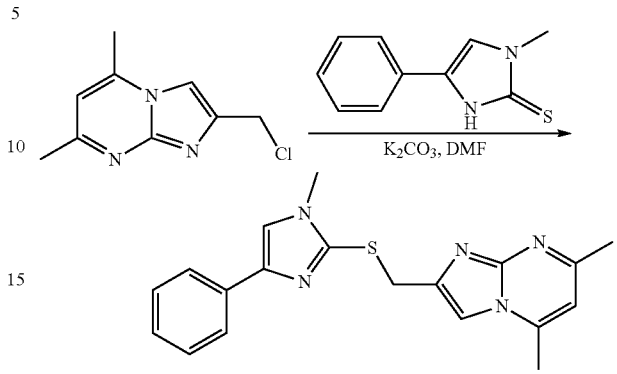

A mixture of 2-chloromethyl-5,7-dimethyl-imidazo[1,2-a]pyrimidine (1.55 g, 0.8 mmol), 1-methyl-4-phenyl-1,3-dihydro-imidazole-2-thione (1.5 g, 0.8 mmol) and K$_2$CO$_3$ (3.31 g, 2.4 mmol) in dry DMF (20 mL) was stirred under N$_2$ at room temperature overnight. After removal of the solvent under vacuum, the residue was purified by preparative HPLC to afford the title compound (1.31 g, 47%) as a white solid. LC-MS: m/z=350.2 (MH$^+$), $t_R$=2.14 min, method D.

The following compounds of the invention were prepared analogously:
5,7-Dimethyl-2-(1-methyl-4-phenyl-1H-imidazol-2-ylsulfanyl methyl)-[1,2,4]triazolo[1,5-a]pyridine. LC-MS: m/z=350.3 (MH$^+$), $t_R$=0.76 min, method A.
2-(1-Methyl-4-phenyl-1H-imidazol-2-ylsulfanylmethyl)-1-phenyl-1H-benzoimidazole (This reaction was run using DIPEA as base). LC-MS: m/z=396.8 (MH$^+$), $t_R$=0.60 min, method C.
2-(1-Methyl-4-phenyl-1H-imidazol-2-ylsulfanylmethyl)-imidazo[1,2-a]pyrimidine (This reaction was run at 70° C. overnight using DIPEA as base). LC-MS: m/z=322.1 (MH$^+$), $t_R$=0.36 min, method C.
8-Methyl-2-(1-methyl-4-phenyl-1H-imidazol-2-ylsulfanylmethyl)-imidazo[1,2-a]pyridine (This reaction was run at 60° C. for 1 h using DIPEA as base). LC-MS: m/z=335.3 (MH$^+$), $t_R$=0.55 min, method A.
2-(1-Methyl-4-phenyl-1H-imidazol-2-ylsulfanylmethyl)-imidazo[1,2-a]pyridine (This reaction was run at 60° C. for 1 h using DIPEA as base). LC-MS: m/z=321.0 (MH$^+$), $t_R$=0.47 min, method A.
8-Methyl-2-(4-phenyl-1H-imidazol-2-ylsulfanylmethyl)-imidazo[1,2-a]pyridine (This reaction was run at 60° C. for 1 h using DIPEA as base). LC-MS: m/z=321.2 (MH$^+$), $t_R$=0.48 min, method A.
2-[4-(3-Methoxy-phenyl)-1-methyl-1H-imidazol-2-ylsulfanylmethyl]-5,7-dimethyl-imidazo[1,2-a]pyrimidine (This reaction was run at 60° C. for 2 h using DIPEA as base). LC-MS: m/z=380.6 (MH$^+$), $t_R$=0.65 min, method A.
5,7-Dimethyl-2-(4-phenyl-1H-imidazol-2-ylsulfanylmethyl)-imidazo[1,2-a]pyrimidine (This reaction was run at 70° C. for 1 h using DIPEA as base). LC-MS: m/z=336.3 (MH$^+$), $t_R$=0.54 min, method A.
5,7-Dimethyl-2-(4-phenyl-1H-imidazol-2-ylsulfanylmethyl)-[1,2,4]triazolo[1,5-a]pyrimidine, LC-MS (MH$^+$): m/z=337.4, $t_R$ (min, method A)=0.58
5,7-Dimethyl-2-(1-methyl-4-phenyl-1H-imidazol-2-ylsulfanylmethyl)-[1,2,4]triazolo[1,5-a]pyrimidine, LC-MS (MH$^+$): m/z=351.4, $t_R$ (min, method A)=0.58

5-Ethyl-2-(1-methyl-4-phenyl-1H-imidazol-2-ylsulfanylmethyl)-[1,2,4]triazolo[1,5-a]pyridine, LC-MS (MH+): m/z=350.5, $t_R$ (min, method A)=0.76

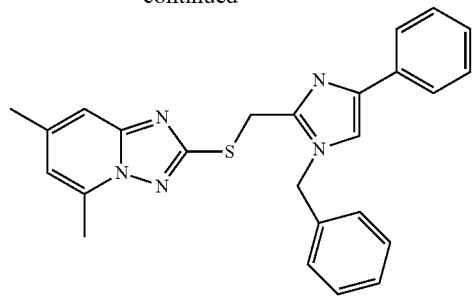

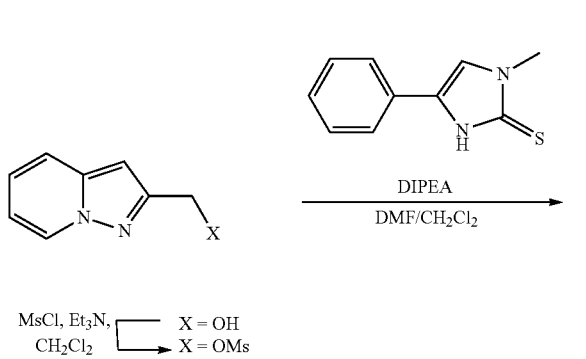

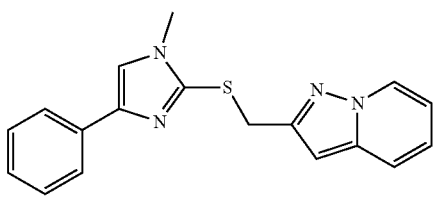

A solution of methanesulfonyl chloride (0.149 g, 0.13 mmol) in dichloromethane (2 mL) was added to a solution of pyrazolo[1,5-a]pyridin-2-yl-methanol (0.148 g, 0.1 mmol) and triethylamine (0.303 g, 0.3 mmol) in dichloromethane (3 mL) at −10° C. under $N_2$. After the addition was complete, the mixture was stirred at −10° C. for 1 h. Ice water (10 mL) was added, and the organic layer was separated, dried over sodium sulfate, filtered and concentrated under vacuum to give methanesulfonic acid pyrazolo[1,5-a]pyridin-2-ylmethyl ester as a yellow oil, which was used for the next step without further purification. A solution of this material (0.22 g, 0.1 mmol) in dry dichloromethane (2 mL) was added to a solution of 1-methyl-4-phenyl-1,3-dihydro-imidazole-2-thione (0.190 g, 0.1 mmol) and DIPEA (0.303 g, 0.3 mmol) in dry DMF (3 mL) at −10° C. under $N_2$. The mixture was stirred at 0° C. for 2 hours, and was then concentrated under reduced pressure. The residue was purified by preparative HPLC to afford the title compound (50 mg, 15%). LC-MS: m/z=321.1 (MH+), $t_R$=2.16 min, method F.

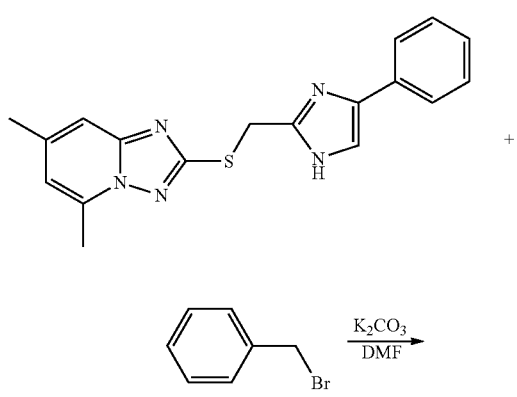

To a solution of 5,7-dimethyl-2-(4-phenyl-1H-imidazol-2-ylmethylsulfanyl)-[1,2,4]triazolo[1,5-a]pyridine (15 mg, 0.045 mmol) in DMF (0.5 mL) was added benzyl bromide (5.4 μL, 0.045 mmol) and potassium carbonate (9.3 mg, 0.067 mmol) and the resulting mixture was stirred overnight at 75° C. Volatiles were evaporated and the residue was purified by preparative LC-MS to yield the title compound. LC-MS: m/z=426.3 (MH+), $t_R$=1.06 min, method A.

The following compounds of the invention were prepared analogously:

2-[1-(4-Chloro-benzyl)-4-phenyl-1H-imidazol-2-ylmethylsulfanyl]-5,7-dimethyl-[1,2,4]triazolo[1,5-a]pyridine. LC-MS: m/z=460.7 (MH+), $t_R$=1.16 min, method A.

5,7-Dimethyl-2-(4-phenyl-1-propyl-1H-imidazol-2-ylsulfanylmethyl)-imidazo[1,2-a]pyrimidine. LC-MS: m/z=378.6 (MH+), $t_R$=0.80 min, method A.

2-(1-Isopropyl-4-phenyl-1H-imidazol-2-ylsulfanylmethyl)-5,7-dimethyl-imidazo[1,2-a]pyrimidine. LC-MS: m/z=378.6 (MH+), $t_R$=0.78 min, method A.

2-(1-Cyclopropylmethyl-4-phenyl-1H-imidazol-2-ylsulfanylmethyl)-5,7-dimethyl-imidazo[1,2-a]pyrimidine. LC-MS: m/z=390.4 (MH+), $t_R$=0.83 min, method A.

5,7-Dimethyl-2-[1-(3-methyl-butyl)-4-phenyl-1H-imidazol-2-ylsulfanylmethyl]-imidazo[1,2-a]pyrimidine. LC-MS: m/z=406.6 (MH+), $t_R$=0.99 min, method A.

2-[2-(5,7-Dimethyl-imidazo[1,2-a]pyrimidin-2-ylmethylsulfanyl)-4-phenyl-imidazol-1-yl]-acetamide. LC-MS: m/z=393.5 (MH+), $t_R$=0.52 min, method A 5,7-Dimethyl-2-[4-phenyl-1-(tetrahydro-pyran-4-ylmethyl)-1H-imidazol-2-ylsulfanylmethyl]-imidazo[1,2-a]pyrimidine. LC-MS: m/z=434.6 (MH+), $t_R$=0.77 min, method A.

[2-(5,7-Dimethyl-[1,2,4]triazolo[1,5-a]pyridin-2-ylsulfanylmethyl)-4-phenyl-imidazol-1-yl]-acetonitrile. LC-MS: m/z=375.2 (MH+), $t_R$=0.70 min, method A.

2-(1-Isopropyl-4-phenyl-1H-imidazol-2-ylmethylsulfanyl)-5,7-dimethyl-[1,2,4]triazolo[1,5-a]pyridine. LC-MS: m/z=378.5 (MH+), $t_R$=0.79 min, method A.

2-(1-Cyclopropylmethyl-4-phenyl-1H-imidazol-2-ylmethylsulfanyl)-5,7-dimethyl-[1,2,4]triazolo[1,5-a]pyridine. LC-MS: m/z=390.5 (MH+), $t_R$=0.85 min, method A.

2-[2-(5,7-Dimethyl-[1,2,4]triazolo[1,5-a]pyridin-2-ylsulfanylmethyl)-4-phenyl-imidazol-1-yl]-acetamide. LC-MS: m/z=393.5 (MH+), $t_R$=0.51 min, method A.

[2-(5,7-Dimethyl-imidazo[1,2-a]pyrimidin-2-ylmethylsulfanyl)-4-phenyl-imidazol-1-yl]-acetonitrile. LC-MS: m/z=375.2 (MH+), $t_R$=0.93 min, method A.

2-(1-Benzyl-4-phenyl-1H-imidazol-2-ylsulfanylmethyl)-5,7-dimethyl-imidazo[1,2-a]pyrimidine. LC-MS: m/z=426.2 (MH+), $t_R$=1.08 min, method A.

2-[1-(4-Chloro-benzyl)-4-phenyl-1H-imidazol-2-ylsulfanylmethyl]-5,7-dimethyl-imidazo[1,2-a]pyrimidine. LC-MS: m/z=460.5 (MH+), $t_R$=1.18 min, method A.

2-(1-Ethyl-4-phenyl-1H-imidazol-2-ylsulfanylmethyl)-5,7-dimethyl-imidazo[1,2-a]pyrimidine. LC-MS: m/z=364.5 (MH+), t_R=0.70 min, method A.

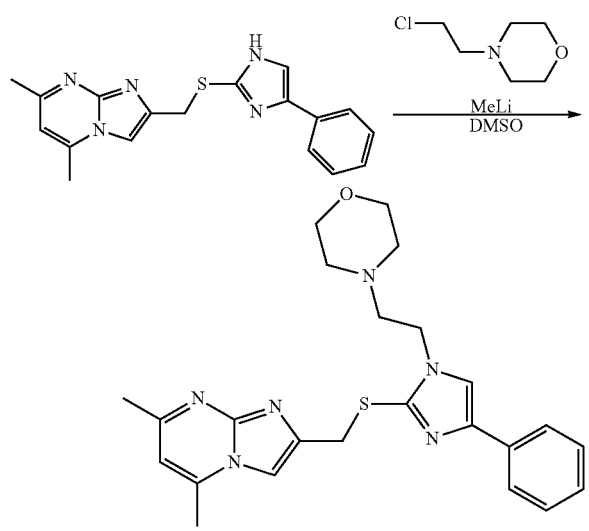

A solution of methyl lithium in ether (1.60 M, 0.205 mL, 0.328 mmol) was added dropwise to dimethyl sulfoxide (2.00 mL, 28.2 mmol) and the mixture left to stir for 40 minutes at room temperature. A solution of 5,7-Dimethyl-2-(4-phenyl-1H-imidazol-2-ylsulfanylmethyl)-imidazo[1,2-a]pyrimidine (0.100 g, 0.298 mmol) and N-(2-chloroethyl)morpholine (0.0666 g, 0.358 mmol) in dimethyl sulfoxide was added dropwise to the generated dimsyl anion. The resulting mixture was stirred at 80° C. for 45 minutes. After cooling to room temperature, water was carefully added and the mixture was extracted with ethyl acetate (20 mL). The combined organic extracts were dried over sodium sulfate and the solvent removed in vacuo. Column chromatography of the crude product using ethyl acetate:methanol (95:5 v/v) gave the product as a yellow oil. It was dissolved in a minimum amount of methanol and ethereal hydrogen chloride was added dropwise to precipitate the hydrochloride salt of title compound as a yellow solid which was collected by filtration and washed with ether (71 mg, 49%). LC-MS: m/z=449.3 (MH+), t_R=0.37 min, method C.

The Following compounds were prepared analogously:
4-(2-(2-((8-chloro-[1,2,4]triazolo[1,5-a]pyridin-2-yl)methylthio)-4-phenyl-1H-imidazol-1-yl)ethyl)morpholine, LC-MS (MH+); m/z=456.0, t_R (min, method A)=2.08
4-(2-(2-((5-chloro-[1,2,4]triazolo[1,5-a]pyridin-2-yl)methylthio)-4-phenyl-1H-imidazol-1-yl)ethyl)morpholine, LC-MS (MH+): m/z=456.0, t_R (min, method A)=2.16
2-(1-Isobutyl-4-phenyl-1H-imidazol-2-ylsulfanylmethyl)-5,7-dimethyl-[1,2,4]triazolo[1,5-a]pyrimidine, LC-MS (MH+): m/z=393.5, t_R (min, method A)=0.88
5,7-Dimethyl-2-[1-(2-morpholin-4-yl-ethyl)-4-phenyl-1H-imidazol-2-ylsulfanylmethyl]-[1,2,4]triazolo[1,5-a]pyrimidine, LC-MS (MH+): m/z=450.6, t_R (min, method A)=0.55
1-{2-[2-(5,7-Dimethyl-[1,2,4]triazolo[1,5-a]pyrimidin-2-ylmethylsulfanyl)-4-phenyl-imidazol-1-yl]-ethyl}-3-methyl-imidazolidin-2-one, LC-MS (MH+): m/z=463.6, t_R (min, method A)=0.66
4-(2-(2-((8-methyl-[1,2,4]triazolo[1,5-a]pyridin-2-yl)methylthio)-4-phenyl-1H-imidazol-1-yl)ethyl)morpholine, LC-MS (MH+): m/z=417.5, t_R (min, method A)=2.26
4-(2-(2-((5-methyl-[1,2,4]triazolo[1,5-a]pyridin-2-yl)methylthio)-4-phenyl-1H-imidazol-1-yl)ethyl)morpholine, LC-MS (MH+): m/z=417.5, t_R (min, method A)=2.22
4-(2-(2-(2-(5,7-dimethyl-[1,2,4]triazolo[1,5-a]pyridin-2-yl)ethyl)-4-phenyl-1H-imidazol-1-yl)ethyl)morpholine, LC-MS (MH+): m/z=431.6, t_R (rin, method A)=2.26
2-(2-(1-ethyl-4-phenyl-1H-imidazol-2-yl)ethyl)-5,7-dimethyl-[1,2,4]triazolo[1,5-a]pyridine, LC-MS (MH+): m/z=346.4, t_R (min, method A)=2.5
5,7-dimethyl-2-(2-(4-phenyl-1-propyl-1H-imidazol-2-yl)ethyl)-[1,2,4]triazolo[1,5-a]pyridine, LC-MS (MH+): m/z=360.5, t_R (min, method A)=2.53
2-[2-(1-Isobutyl-4-phenyl-1H-imidazol-2-yl)-ethyl]-5-methyl-[1,2,4]triazol[1,5-a]pyridine, LC-MS (MH+): m/z=360.5, t_R (min, method A)=0.88
2-[2-(1-Isopropyl-4-phenyl-Imidazol-2-yl)-ethyl]-5-methyl-[1,2,4]triazolo[1,5-a]pyridine, LC-MS (MH+): m/z=346.4, t_R (min, method A)=0.79
1-Methyl-3-(2-{2-[2-(5-methyl-[1,2,4]triazolo[1,5-a]pyridin-2-yl)-ethyl]-4-phenyl-imidazol-1-yl}-ethyl)-imidazolidin-2-one, LC-MS (MH+): m/z=430.5, t_R (min, method A)=0.99
5-Methyl-2-{2-[4-phenyl-1-(3-piperidin-1-yl-propyl)-1H-imidazol-2-yl]-ethyl}-[1,2,4]triazolo[1,5-a]pyridine, LC-MS (MH+): m/z=429.6, t_R (min, method A)=0.38
5,7-Dimethyl-2-{2-[4-phenyl-1-(2-piperidin-1-yl-ethyl)-1H-imidazol-2-yl]-ethyl}-[1,2,4]triazolo[1,5-a]pyrimidine, LC-MS (MH+): m/z=430.6, t_R (min, method A)=0.46
2-[2-(1-Isobutyl-4-phenyl-1H-imidazol-2-yl)-ethyl]-5,7-dimethyl-[1,2,4]triazolo[1,5-a]pyrimidine, LC-MS (MH+): m/z=375.5, t_R (min, method A)=0.8
2-[2-(1-Isopropyl-4-phenyl-1H-imidazol-2-yl)-ethyl]-5,7-dimethyl-[1,2,4]triazolo[1,5-a]pyrimidine, LC-MS (MH+): m/z=361.5, t_R (min, method A)=0.7
1-(2-{2-[2-(5,7-Dimethyl-[1,2,4]triazolo[1,5-a]pyrimidin-2-yl)-ethyl]-4-phenyl-imidazol-1-yl}-ethyl)-3-methyl-imidazolidin-2-one, LC-MS (MH+): m/z=445.5, t_R (min, method A)=0.61
5,7-Dimethyl-2-{2-[1-(2-morpholin-4-yl-ethyl)-4-phenyl-1H-imidazol-2-yl]-ethyl}-[1,2,4]triazolo[1,5-a]pyrimidine, LC-MS (MH+): m/z=432.5, t_R (min, method A)=0.44
5,7-Dimethyl-2-[2-(4-phenyl-1-propyl-1H-imidazol-2-yl)-ethyl]-[1,2,4]triazolo[1,5-a]pyrimidine, LC-MS (MH+): m/z=361.5, t_R (min, method A)=0.71

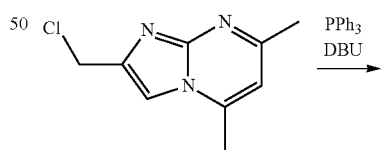

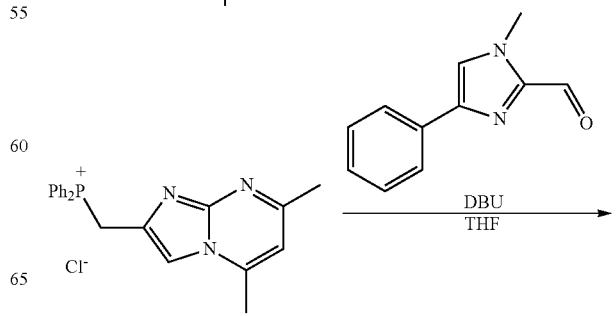

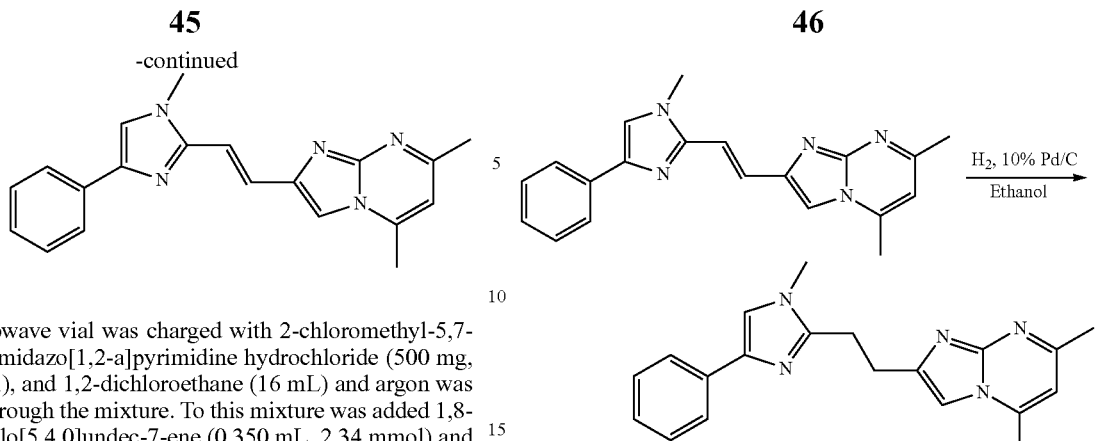

A microwave vial was charged with 2-chloromethyl-5,7-dimethyl-imidazo[1,2-a]pyrimidine hydrochloride (500 mg, 2.15 mmol), and 1,2-dichloroethane (16 mL) and argon was bubbled through the mixture. To this mixture was added 1,8-diazabicyclo[5.4.0]undec-7-ene (0.350 mL, 2.34 mmol) and triphenylphosphine (848 mg, 3.23 mmol). The vial was sealed with a crimp-on cap and the mixture was heated at 140° C. for 1 hour using a microwave synthesizer. Evaporation of volatiles afforded crude (5,7-dimethyl-imidazo[1,2-a]pyrimidin-2-ylmethyl)-triphenyl-phosphonium chloride as a dark grey solid (1.976 g) which was used without purification.

A solution of 1-methyl-4-phenyl-1H-imidazole-2-carbaldehyde (109 mg, 0.585 mmol) in dry THF was added to (5,7-dimethyl-imidazo[1,2-a]pyrimidin-2-ylmethyl)-triphenyl-phosphonium chloride (536 mg, 0.585 mmol) under argon and 1,8-diazabicyclo[5.4.0]undec-7-ene (87.5 μL, 0.585 mmol) was added. The reaction mixture was stirred at room temperature for 3 days after which it was evaporated onto Celite®. Silica gel chromatography (gradient elution; A:B 0:100→100:0, where A is 10% methanol in ethyl acetate and B is heptane) afforded a mixture of the title compound and the phosphonium starting material. This mixture was dissolved in dry THF and was re-submitted to the reaction conditions using 120 mg of aldehyde and 90 μl of diazabicyclo[5.4.0]undec-7-ene with an overnight reaction time at room temperature. Chromatography using the conditions above afforded the title compound (35 mg, 18%) as a brown solid. LC-MS: m/z=329.8 (MH$^+$), $t_R$=0.36 min, method C.

The Following compounds were prepared analogously:
8-Methyl-2-[(2-(1-methyl-4-phenyl-1H-imidazol-2-yl)-vinyl]-[1,2,4]triazolo[1,5-a]pyridine
5-Methyl-2-[2-(1-methyl-4-phenyl-1H-imidazol-2-yl)-vinyl]-[1,2,4]triazolo[1,5-a]pyridine
5,7-dimethyl-2-(2-(1-methyl-4-phenyl-1H-imidazol-2-yl)vinyl)-[1,2,4]triazolo[1,5-a]pyridine
6,8-dimethyl-2-(2-(1-methyl-4-phenyl-1H-imidazol-2-yl)vinyl)-[1,2,4]triazolo[1,5-a]pyridine
5,7-dimethyl-2-(2-(4-phenyl-1H-imidazol-2-yl)vinyl)-[1,2,4]triazolo[1,5-a]pyridine
5,7-Dimethyl-2-[2-(1-methyl-4-phenyl-1H-imidazol-2-yl)-vinyl]-[1,2,4]triazolo[1,5-a]pyrimidine
5,7-Dimethyl-2-[2-(4-phenyl-1H-imidazol-2-yl)-vinyl]-[1,2,4]triazolo[1,5-a]pyrimidine
5,8-Dimethyl-2-[2-(1-methyl-4-phenyl-1H-imidazol-2-yl)-vinyl]-[1,2,4]triazolo[1,5-a]pyrimidine
5-Methyl-2-[2-(4-phenyl-1H-imidazol-2-yl)-vinyl]-[1,2,4]triazolo[1,5-a]pyridine
5,6,7-Trimethyl-2-[2-(1-methyl-4-phenyl-1H-imidazol-2-yl)-vinyl]-[1,2,4]triazolo[1,5-a]pyrimidine
5-Methyl-2-[2-(1-methyl-4-phenyl-1H-imidazol-2-yl)-vinyl]-7-phenyl-[1,2,4]triazolo[1,5-a]pyrimidine
5-Methyl-2-{2-[4-phenyl-1-(2-piperidin-1-yl-ethyl)-1H-imidazol-2-yl]-vinyl}-[1,2,4]triazolo[1,5-a]pyridine To a solution of trans-5,7-dimethyl-2-[(E)-2-(1-methyl-4-phenyl-1H-imidazol-2-yl)-vinyl]-imidazo[1,2-a]pyrimidine (13.0 mg, 0.0395 mmol) in ethanol (4 mL) was added 10% palladium on carbon (9 mg), optionally, a catalytic amount of acid e.g. trifluoracetic acid, can be added. A current of hydrogen gas was bubbled through, and the reaction was kept under an atmosphere of hydrogen overnight with stirring. Filtration and evaporation of volatiles afforded the title compound (9.8 mg, 75%). LC-MS: m/z=332.3 (MH$^+$), $t_R$=0.37 min, method A.

The Following compounds were prepared analogously:
8-Methyl-2-[2-(1-methyl-4-phenyl-1H-imidazol-2-yl)-ethyl]-[1,2,4]triazolo[1,5-a]pyridine, LC-MS (MH$^+$): m/z=318.4, tR (min, method A)=2.2
5-Methyl-2-[2-(1-methyl-4-phenyl-1H-imidazol-2-yl)-ethyl]-[1,2,4]triazolo[1,5-a]pyridine, LC-MS (MH$^+$): m/z=318.4, tR (min, method A)=2.44
5,7-dimethyl-2-(2-(1-methyl-4-phenyl-1H-imidazol-2-yl)ethyl)-[1,2,4]triazolo[1,5-a]pyridine, LC-MS (MH$^+$): m/z=332.4, tR (min, method A)=2.57
6,8-dimethyl-2-(2-(1-methyl-4-phenyl-1H-imidazol-2-yl)ethyl)-[1,2,4]triazolo[1,5-a]pyridine, LC-MS (MH$^+$): m/z=332.4, tR (min, method A)=2.65
5,7-dimethyl-2-(2-(4-phenyl-1H-imidazol-2-yl)ethyl)-[1,2,4]triazolo[1,5-a]pyridine LC-MS (MH$^+$): m/z=318A, tR (min, method A)=2.61
5,7-Dimethyl-2-[2-(1-methyl-4-phenyl-1H-imidazol-2-yl)-ethyl]-[1,2,4]triazolo[1,5-a]pyrimidine, LC-MS (MH$^+$): m/z=333.4, tR (min, method A)=0.57
5,7-Dimethyl-2-[2-(4-phenyl-1H-imidazol-2-yl)-ethyl]-[1,2,4]triazolo[1,5-a]pyrimidine, LC-MS (MH$^+$): m/z=319.4, tR (min, method A)=0.57
5,8-Dimethyl-2-[2-(1-methyl-4-phenyl-1H-imidazol-2-yl)-ethyl]-[1,2,4]triazolo[1,5-a]pyrimidine, LC-MS (MH$^+$): m/z=332.4, tR (min, method A)=0.71
5-Methyl-2-[2-(4-phenyl-1H-imidazol-2-yl)-ethyl]-[1,2,4]triazolo[1,5-a]pyridine, LC-MS (MH$^+$): m/z=304.4, tR (min, method A)=0.6
5,6,7-Trimethyl-2-[2-(1-methyl-4-phenyl-1H-imidazol-2-yl)-ethyl]-[1,2,4]triazolo[1,5-a]pyrimidine, LC-MS (MH$^+$): m/z=347.4, tR (min, method A)=0.63
5-Methyl-2-[2-(1-methyl-4-phenyl-1H-imidazol-2-yl)-ethyl]-7-phenyl-[1,2,4]triazolo[1,5-a]pyrimidine, LC-MS (MH$^+$): m/z=395.5, tR (min, method A)=0.8
5-Methyl-2-(2-[4-phenyl-1-(2-piperidin-1-yl-ethyl)-1H-imidazol-2-yl]-ethyl)-[1,2,4]triazolo[1,5-a]pyridine, LC-MS (MH$^+$): m/z=415.6, tR (min, method A)=0.5

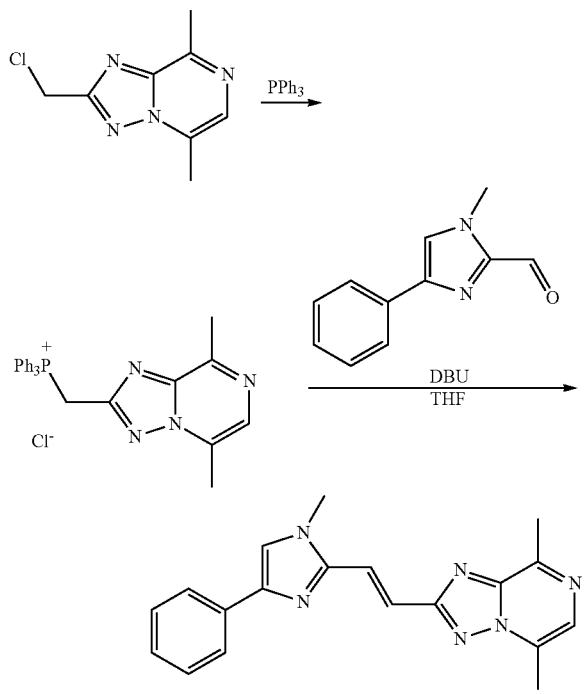

A solution of 2-chloromethyl-5,8-dimethyl-[1,2,4]triazolo[1,5-a]pyrazine (1.351 g, 6.87 mmol) and triphenylphosphine (1.80 g, 6.87 mmol) in acetonitrile 150 mL was heated at reflux for 12 h. The solvents were removed in vacuo and the residue slurried in ether, filtered and dried to yield (5,8-Dimethyl-[1,2,4]triazolo[1,5-a]pyrazin-2-ylmethyl)-triphenyl-phosphonium; chloride as an off white solid (2.412 g, 74.9%). LC-MS: m/z=423.2 ([M-Cl]+), tR=0.86 min, method A.

A solution of 1-methyl-4-phenyl-1H-imidazole-2-carbaldehyde (220 mg, 1.18 mmol) in dry THF was added to (5,8-Dimethyl-[1,2,4]triazolo[1,5-a]pyrazin-2-ylmethyl)-triphenyl-phosphonium; chloride (500 mg, 1.18 mmol) under argon and 1,8-diazabicyclo[5.4.0]undec-7-ene (176 µL, 1.18 mmol) was added. The reaction mixture was stirred at room temperature for 2 h after which it was evaporated onto silica gel (2 g). Silica gel chromatography (gradient elution; A:B 50:50→100:0, where A is ethyl acetate and is heptane) afforded the title compound (334 mg, 79%) as an off white solid. LC-MS: m/z=331.4 (MH+), $t_R$=0.65 min, method A.

The Following compounds were prepared analogously and were used for the preparation of final compounds without prior purification or characterization:
trans-1-{2-[2-(5,7-Dimethyl-[1,2,4]triazolo[1,5-a]pyrimidin-2-yl)-vinyl]-4-phenyl-imidazol-1-yl}-propan-2-ol
trans-(S)-1-{2-[2-(5,7-Dimethyl-[1,2,4]triazolo[1,5-a]pyrimidin-2-yl)-vinyl]-4-phenyl-imidazol-1-yl}-propan-2-ol
trans-8-methoxy-5-methyl-2-(2-(1-methyl-4-phenyl-1H-imidazol-2-yl)vinyl)-[1,2,4]triazolo[1,5-a]pyridine
trans-(R)-1-{2-[2-(5,7-Dimethyl-[1,2,4]triazolo[1,5-a]pyrimidin-2-yl)-vinyl]-4-phenyl-imidazol-1-yl}-propan-2-ol
trans-8-fluoro-2-(2-(1-methyl-4-phenyl-1H-imidazol-2-yl)vinyl)-[1,2,4]triazolo[1,5-a]pyridine
trans-1-{2-[2-(5,7-Dimethyl-[1,2,4]triazolo[1,5-a]pyrimidin-2-yl)-vinyl]-4-phenyl-imidazol-1-yl}-2-methyl-propan-2-ol
trans-8-Ethyl-5-methyl-2-[2-(1-methyl-4-phenyl-1H-imidazol-2-yl)-vinyl]-[1,2,4]triazolo[1,5-c]pyrimidine
trans-5-Methyl-2-[2-(1-methyl-4-phenyl-1H-imidazol-2-yl)-vinyl]-7-propyl-[1,2,4]triazolo[1,5-a]pyrimidine
trans-7-Methoxy-5-methyl-2-[2-(1-methyl-4-phenyl-1H-imidazol-2-yl)-vinyl]-[1,2,4]triazolo[1,5-c]pyrimidine
trans-7-Isopropyl-5-methyl-2-[2-(1-methyl-4-phenyl-1H-imidazol-2-yl)-vinyl]-[1,2,4]triazolo[1,5-a]pyrimidine
trans-2-{2-[4-(2,4-Difluoro-phenyl)-1-methyl-1H-imidazol-2-yl]-vinyl}-5,7-dimethyl-[1,2,4]triazolo[1,5-a]pyrimidine
trans-7-Methoxy-5,8-dimethyl-2-[2-(1-methyl-4-phenyl-1H-imidazol-2-yl)-vinyl]-[1,2,4]triazolo[1,5-c]pyrimidine
trans-5,8-Dimethyl-2-[2-(1-methyl-4-phenyl-1H-imidazol-2-yl)-vinyl]-[1,2,4]triazolo[1,5-c]pyrimidine
trans-2-{2-[4-(2-Methoxy-phenyl)-1-methyl-1H-imidazol-2-yl]-vinyl}-5,7-dimethyl-[1,2,4]triazolo[1,5-a]pyrimidine
trans-{5-Methyl-2-[2-(1-methyl-4-phenyl-1H-imidazol-2-yl)-vinyl]-[1,2,4]triazolo[1,5-a]pyrimidin-7-yl}-methanol
trans-8-Ethyl-5-methyl-2-[2-(1-methyl-4-phenyl-1H-imidazol-2-yl)-vinyl]-[1,2,4]triazolo[1,5-a]pyridine
trans-5,8-Dimethoxy-2-[2-(1-methyl-4-phenyl-1H-imidazol-2-yl)-vinyl]-[1,2,4]triazolo[1,5-a]pyridine

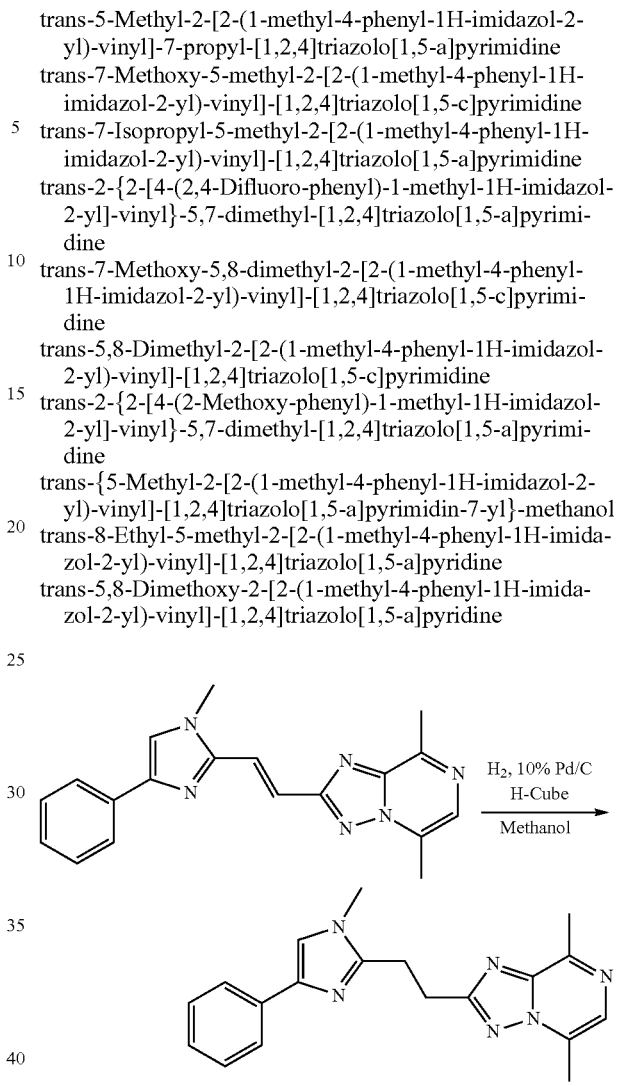

A solution of trans-5,8-dimethyl-2-[(E)-2-(1-methyl-4-phenyl-1H-imidazol-2-yl)-vinyl]-imidazo[1,2-a]pyrazine (330 mg, 1.0 mmol) in methanol (50 mL) was passed through a H-Cube® Continuous-flow Hydrogenation Reactor (ThalesNano) at a flow rate of 1 mL/min through a small cartridge of 10% Pd/C (THS01111) with an internal temperature of 25° C. and 1 bar of hydrogen pressure. Evaporation of the volatiles afforded the title compound (178 mg, 51%). LC-MS: m/z=333.2 (MH+), $t_R$=0.57 min, method A.

The Following compounds were prepared analogously:
5,8-Dimethyl-2-[2-(1-methyl-4-phenyl-1H-imidazol-2-yl)-ethyl]-imidazo[1,2-c]pyrimidine, LC-MS: m/z=333.2 (MH+), $t_R$=0.67 min, method E.
1-{2-[2-(5,7-Dimethyl-[1,2,4]triazolo[1,5-a]pyrimidin-2-yl)-ethyl]-4-phenyl-imidazol-1-yl}-propan-2-ol, LC-MS: m/z=377.4 (MH+), $t_R$=0.58 min, method A.
(S)-1-{2-[2-(5,7-Dimethyl-[1,2,4]triazolo[1,5-a]pyrimidin-2-yl)-ethyl]-4-phenyl-imidazol-1-yl}-propan-2-ol, LC-MS: m/z=377.4 (MH+), $t_R$=0.58 min, method A.
(R)-1-(2-[2-(5,7-Dimethyl-[1,2,4]triazolo[1,5-a]pyrimidin-2-yl)-ethyl]-4-phenyl-imidazol-1-yl}-propan-2-ol, LC-MS: m/z=377.4 (MH+), $t_R$=0.59 min, method A.
1-{2-[2-(5,7-Dimethyl-[1,2,4]triazolo[1,5-a]pyrimidin-2-yl)-ethyl]-4-phenyl-imidazol-1-yl}-2-methyl-propan-2-ol, LC-MS: m/z=391.8 (MH+), $t_R$=0.64 min, method A.

8-methoxy-5-methyl-2-(2-(1-methyl-4-phenyl-1H-imidazol-2-yl)ethyl)-[1,2,4]triazolo[1,5-a]pyridine, LC-MS: m/z=348.4 (MH$^+$), $t_R$=0.77 min, method E.

8-fluoro-2-(2-(1-methyl-4-phenyl-1H-imidazol-2-yl)ethyl)-[1,2,4]triazolo[1,5-a]pyridine, LC-MS: m/z=322.4 (MH$^+$), $t_R$=0.60 min, method A.

8-Ethyl-5-methyl-2-[2-(1-methyl-4-phenyl-1H-imidazol-2-yl)-ethyl]-[1,2,4]triazolo[1,5-c]pyrimidine, LC-MS: m/z=347.4 (MH$^+$), $t_R$=0.67 min, method A.

5-Methyl-2-[2-(1-methyl-4-phenyl-1H-imidazol-2-yl)-ethyl]-7-propyl-[1,2,4]triazolo[1,5-a]pyrimidine, LC-MS: m/z=361.5 (MH$^+$), $t_R$=0.74 min, method A.

7-Methoxy-5-methyl-2-[2-(1-methyl-4-phenyl-1H-1-imidazol-2-yl)-ethyl]-[1,2,4]triazolo[1,5-c]pyrimidine, LC-MS: m/z=349.4 (MH$^+$), $t_R$=0.63 min, method A.

7-Isopropyl-5-methyl-2-[2-(1-methyl-4-phenyl-1H-imidazol-2-yl)-ethyl]-[1,2,4]triazolo[1,5-a]pyrimidine, LC-MS: m/z=361.5 (MH$^+$), $t_R$=0.74 min, method A.

2-{2-[4-(2,4-Difluoro-phenyl)-1-methyl-1H-imidazol-2-yl]-ethyl}-5,7-dimethyl-[1,2,4]triazolo[1,5-a]pyrimidine, LC-MS: m/z=369.4 (MH$^+$), $t_R$=0.64 min, method A.

7-Methoxy-5,8-dimethyl-2-[2-(1-methyl-4-phenyl-1H-imidazol-2-yl)-ethyl]-[1,2,4]triazolo[1,5-c]pyrimidine, LC-MS: m/z=363.4 (MH$^+$), $t_R$=0.78 min, method A.

5,8-Dimethyl-2-[2-(1-methyl-4-phenyl-1H-imidazol-2-yl)-ethyl]-[1,2,4]triazolo[1,5-c]pyrimidine, LC-MS: m/z=333.4 (MH$^+$), $t_R$=0.58 min, method A.

2-{(2-[4-(2-Methoxy-phenyl)-1-methyl-1H-imidazol-2-yl]-ethyl}-5,7-dimethyl-[1,2,4]triazolo[1,5-a]pyrimidine, LC-MS: m/z=363.4 (MH$^+$), $t_R$=0.62 min, method A.

{5-Methyl-2-[2-(1-methyl-4-phenyl-1H-imidazol-2-yl)-ethyl]-[1,2,4]triazolo[1,5-a]pyrimidin-7-yl}-methanol, LC-MS: m/z=349.4 (MH$^+$), $t_R$=0.47 min, method A.

8-Ethyl-5-methyl-2-[2-(1-methyl-4-phenyl-1H-imidazol-2-yl)-ethyl]-[1,2,4]triazolo[1,5-a]pyridine, LC-MS: m/z=346.4 (MH$^+$), $t_R$=0.93 min, method E.

5,8-Dimethoxy-2-[2-(1-methyl-4-phenyl-1H-imidazol-2-yl)-ethyl]-[1,2,4]triazolo[1,5-a]pyridine, LC-MS: m/z=364.4 (MH$^+$), $t_R$=0.70 min, method E.

Pharmacological Testing

PDE10A Enzyme

Active PDE10A enzyme is prepared in a number of ways for use in PDE assays (Loughney, K. et al. *Gene* 1999, 234, 109-117; Fujishige, K. et al. *Eur J Biochem.* 1999, 266, 1118-1127 and Soderling, S. et al. *Proc. Natl. Acad. Sci.* 1999, 96, 7071-7076). PDE10A can be expressed as full-length proteins or as truncated proteins, as long as they express the catalytic domain. PDE10A can be prepared in different cell types, for example insect cells or *E. coli*. An example of a method to obtain catalytically active PDE10A is as follows: The catalytic domain of human PDE10A (amino acids 440-779 from the sequence with accession number NP 006652) is amplified from total human brain total RNA by standard RT-PCR and is cloned into the BamH1 and Xho1 sites of the pET28a vector (Novagen). Expression in coli is performed according to standard protocols. Briefly, the expression plasmids are transformed into the BL21(DE3) *E. coli* strain, and 50 mL cultures inoculated with the cells allowed to grow to an OD600 of 0.4-0.6 before protein expression is induced with 0.5 mM IPTG. Following induction, the cells are incubated overnight at room temperature, after which the cells are collected by centrifugation. Cells expressing PDE10A are resuspended in 12 mL (50 mM TRIS-HCl-pH8.0, 1 mM MgCl$_2$ and protease inhibitors). The cells are lysed by sonication, and after all cells are lysed, TritonX100 is added according to Novagen protocols. PDE10A is partially purified on Q sepharose and the most active fractions were pooled.

PDE10A inhibition Assay

A PDE10A assay may for example, be performed as follows: The assay is performed in 60 uL samples containing a fixed amount of the relevant PDE enzyme (sufficient to convert 20-25% of the cyclic nucleotide substrate), a buffer (50 mM HEPES7.6; 10 mM MgCl$_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and IC$_{50}$ values can be calculated using the Xlfit extension to EXCEL.

In the context of the present invention the assay was performed in 60 uL assay buffer (50 mM HEPES pH 7.6; 10 mM MgCl$_2$; 0.02% Tween20) containing enough PDE10A to convert 20-25% of 10 nM $^3$H-cAMP and varying amounts of inhibitors. Following a 1 hour incubation the reactions were terminated by addition of 15 uL 8 mg/mL yttrium silicate SPA beads (Amersham). The beads were allowed to settle for one hr in the dark before the plates were counted in a Wallac 1450 Microbeta counter. IC$_{50}$ values were calculated by non linear regression using XLfit (IDBS).

Results of the experiments showed that the tested compounds of the invention inhibit the PDE10A enzyme with IC$_{50}$ values below 700 nM.

Results of the experiments showed that the majority of the compounds of the invention had IC$_{50}$ values of <1500 nM, many compounds <100 nM, some compounds <50 nM and some had IC$_{50}$ values <10 nM.

Phencyclidine (PCP) Induced Hyperactivity

Male mice (NMRI, Charles River) weighing 20-25 g are used. Eight mice are used in each group receiving the test compound (5 mg/kg) plus PCP (2.3 mg/kg) including the parallel control groups receiving the vehicle of the test compound plus PCP or vehicle injections only. The injection volume is 10 ml/kg. The experiment is made in normal light conditions in an undisturbed room. The test substance is injected per oss 60 min before injection of PCP, which is administered subcutaneous.

Immediately after injection of PCP the mice are placed individually in special designed test cage (20 cm×32 cm). The activity is measured by 5×8 infrared light sources and photocells spaced by 4 cm. The light beams cross the cage 1.8 cm above the bottom of the cage. Recording of a motility count requires interruption of adjacent light beams, thus avoiding counts induced by stationary movements of the mice.

Motility is recorded in 5 min intervals for a period of 1 hour. The drug effect is calculated on the total counts during the 1 hour behavioral test period in the following manner: The mean motility induced by vehicle treatment in the absence of PCP is used as baseline. The 100 percent effect of PCP is accordingly calculated to be total motility counts minus baseline. The response in groups receiving test compound is thus determined by the total motility counts minus baseline, expressed in percent of the similar result recorded in the parallel PCP control group. The percent responses are converted to percent inhibition.

Results of the experiments showed that the tested compounds of the invention are in vivo active compounds that inhibit the PCP induced hyperactivity to the % shown in table 2 above.

What is claimed is:

1. A compound having the structure I

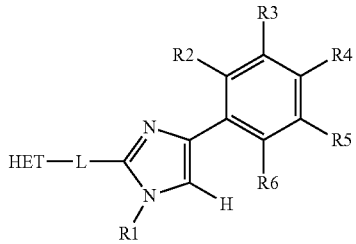

wherein HET is selected from the group consisting of [1,2,4]triazolo[1,5-a]pyridine, imidazo[1,2-a]pyridine, pyrazolo[1,5-a]pyridine, 5,7-dimethyl-[1,2,4]triazolo[1,5-a]pyridine, 5,7-dimethyl-imidazo[1,2-a]pyridine, 5-chloro-imidazo[1,2-a]pyridine, 5-methyl-imidazo[1,2-a]pyridine, 5-trifluoromethyl-imidazo[1,2-a]pyridine, 6-Bromo-5,7-dimethyl-[1,2,4]triazolo[1,5-a]pyridine, 6-bromo-7-methyl-[1,2,4]triazolo[1,5-a]pyridine, 6-chloro-8-methyl-[1,2,4]triazolo[1,5-a]pyridine, 6-chloro-imidazo[1,2-a]pyridine, 7-methyl-[1,2,4]triazolo[1,5-a]pyridine and 8-methyl-imidazo[1,2-a]pyridine, -L- is a linker selected from —$CH_2$—$CH_2$—, —S—$CH_2$—, —$CH_2$—S— or —CH=CH—, $R_1$ is selected from H, $C_1$-$C_6$ alkyl; $C_1$-$C_6$ alkyl($C_3$-$C_8$) cycloalkyl; $C_1$-$C_6$ hydroxyalkyl, $CH_2CN$, $CH_2C(O)NH_2$, $C_1$-$C_6$ arylalkyl, and $C_1$-$C_6$ alkyl-heterocycloalkyl, $R_2$-$R_6$ are selected individually from H, $C_1$-$C_6$ alkoxy and halogen, and tautomers and pharmaceutically acceptable acid addition salts thereof, and polymorphic forms thereof.

2. The compound of claim 1 in which HET is [1,2,4]triazolo[1,5-a]pyridine-6-carbonitrile or imidazo[1,2-a]pyridine-7-carbonitrile.

3. The compound of claim 1, wherein -L- is —$CH_2$—$CH_2$—.

4. The compound of claim 1, wherein -L- is —$CH_2$—S—.

5. The compound of claim 1, wherein -L- is —S—$CH_2$—.

6. The compound of claim 1, wherein -L- is —CH=CH—.

7. The compound of claim 1, wherein R1 is hydrogen.

8. The compound of claim 1, wherein R1 is not hydrogen.

9. The compound of claim 1, wherein $R_2$, $R_3$, $R_4$, $R_5$ and $R_6$ are all hydrogen.

10. The compound of claim 1, wherein at least one of $R_2$, $R_3$, $R_4$, $R_5$ and $R_6$ is $C_1$-$C_6$ alkoxy.

11. The compound of claim 1, wherein at least one of $R_2$, $R_3$, $R_4$, $R_5$ and $R_6$ is halogen.

12. The compound of claim 1, wherein $R_7$, $R_8$ and $R_9$ are all hydrogen.

13. The compound of claim 1, wherein at least one of $R_7$, $R_8$ and $R_9$ is $C_1$-$C_6$ alkyl.

14. The compound of claim 1, wherein at least one of $R_7$, $R_8$ and $R_9$ is $C_1$-$C_6$ alkoxy.

15. The compound of claim 1, wherein at least one of $R_7$, $R_8$ and $R_9$ is halogen.

16. The compound of claim 1, wherein the compound is selected from the group consisting of:

5,7-Dimethyl-2-(1-methyl-4-phenyl-1H-imidazol-2-ylsulfanylmethyl)-[1,2,4]triazolo[1,5-a]pyridine;

2-(1-Cyclopropylmethyl-4-phenyl-1H-imidazol-2-ylmethylsulfanyl)-5,7-dimethyl-[1,2,4]triazolo[1,5-a]pyridine;

2-(1-Benzyl-4-phenyl-1H-imidazol-2-ylmethylsulfanyl)-5,7-dimethyl-[1,2,4]triazolo[1,5-a]pyridine;

5,7-Dimethyl-2-(1-methyl-4-phenyl-1H-imidazol-2-ylmethylsulfanyl)-[1,2,4]triazolo[1,5-a]pyridine;

5,7-Dimethyl-2-(4-phenyl-1H-imidazol-2-ylmethylsulfanyl)-[1,2,4]triazolo[1,5-a]pyridine;

2-(1-Methyl-4-phenyl-1H-imidazol-2-ylsulfanylmethyl)-5-trifluoromethyl-imidazo[1,2-a]pyridine;

2-(1-Ethyl-4-phenyl-1H-imidazol-2-ylmethylsulfanyl)-5,7-dimethyl-[1,2,4]triazolo[1,5-a]pyridine;

[2-(5,7-Dimethyl-[1,2,4]triazolo[1,5-a]pyridin-2-ylsulfanylmethyl)-4-phenyl-imidazol-1-yl]-acetonitrile;

2-(1-Isopropyl-4-phenyl-1H-imidazol-2-ylmethylsulfanyl)-5,7-dimethyl-[1,2,4]triazolo[1,5-a]pyridine;

2-(1-Methyl-4-phenyl-1H-imidazol-2-ylmethylsulfanyl)-[1,2,4]triazolo[1,5-a]pyridine;

2-(4-Phenyl-1H-imidazol-2-ylmethylsulfanyl)-[1,2,4]triazolo[1,5-a]pyridine;

6-Chloro-8-methyl-2-(1-methyl-4-phenyl-1H-imidazol-2-ylmethylsulfanyl)-[1,2,4]triazolo[1,5-a]pyridine;

2-[4-(3-Fluoro-phenyl)-1-methyl-1H-imidazol-2-ylmethylsulfanyl]-5,7-dimethyl-[1,2,4]triazolo[1,5-a]pyridine;

5,7-Dimethyl-2-(1-methyl-4-phenyl-1H-imidazol-2-ylsulfanylmethyl)-imidazo[1,2-a]pyridine;

2-[4-(3-Methoxy-phenyl)-1-methyl-1H-imidazol-2-ylmethylsulfanyl]-5,7-dimethyl-[1,2,4]triazolo[1,5-a]pyridine;

7-Methyl-2-(1-methyl-4-phenyl-1H-imidazol-2-ylmethylsulfanyl)-[1,2,4]triazolo[1,5-a]pyridine;

2-[4-(3-Chloro-phenyl)-1-methyl-1H-imidazol-2-ylmethylsulfanyl]-5,7-dimethyl-[1,2,4]triazolo[1,5-a]pyridine;

2-[4-(4-Fluoro-phenyl)-1-methyl-1H-imidazol-2-ylmethylsulfanyl]-5,7-dimethyl-[1,2,4]triazolo[1,5-a]pyridine;

2-[2-(5,7-Dimethyl-[1,2,4]triazolo[1,5-a]pyridin-2-ylsulfanylmethyl)-4-phenyl-imidazol-1-yl]-acetamide;

5-Chloro-2-(1-methyl-4-phenyl-1H-imidazol-2-ylsulfanylmethyl)-imidazo[1,2-a]pyridine;

8-Methyl-2-(1-methyl-4-phenyl-1H-imidazol-2-ylsulfanylmethyl)-imidazo[1,2-a]pyridine;

2-[4-(2-Fluoro-phenyl)-1-methyl-1H-imidazol-2-ylmethylsulfanyl]-5,7-dimethyl-[1,2,4]triazolo[1,5-a]pyridine;

2-[4-(2-Chloro-phenyl)-1-methyl-1H-imidazol-2-ylmethylsulfanyl]-5,7-dimethyl-[1,2,4]triazolo[1,5-a]pyridine;

2-(1-Ethyl-4-phenyl-1H-imidazol-2-ylmethylsulfanyl)-[1,2,4]triazolo[1,5-a]pyridine;

2-[4-(2-Methoxy-phenyl)-1-methyl-1H-imidazol-2-ylmethylsulfanyl]-5,7-dimethyl-[1,2,4]triazolo[1,5-a]pyridine;

2-(1-Methyl-4-phenyl-1H-imidazol-2-ylsulfanylmethyl)-imidazo[1,2-a]pyridine-7-carbonitrile;

2-(1-Isopropyl-4-phenyl-1H-imidazol-2-ylmethylsulfanyl)-[1,2,4]triazolo[1,5-a]pyridine;

2-[1-(4-Chloro-benzyl)-4-phenyl-1H-imidazol-2-ylmethylsulfanyl]-5,7-dimethyl-[1,2,4]triazolo[1,5-a]pyridine;

6-Bromo-5,7-dimethyl-2-(1-methyl-4-phenyl-1H-imidazol-2-ylmethylsulfanyl)-[1,2,4]triazolo[1,5-a]pyridine;

2-[4-(3-Fluoro-phenyl)-1-methyl-1H-imidazol-2-ylmethylsulfanyl]-[1,2,4]triazolo[1,5-a]pyridine;

2-(1-Methyl-4-phenyl-1H-imidazol-2-ylsulfanylmethyl)-pyrazolo[1,5-a]pyridine;

5-Methyl-2-(1-methyl-4-phenyl-1H-imidazol-2-ylsulfanylmethyl)-imidazo[1,2-a]pyridine;
2-[4-(4-Fluoro-phenyl)-1-methyl-1H-imidazol-2-ylmethylsulfanyl]-[1,2,4]triazolo[1,5-a]pyridine;
2-[4-(3-Chloro-phenyl)-1-methyl-1H-imidazol-2-ylmethylsulfanyl]-[1,2,4]triazolo[1,5-a]pyridine;
2-(6-Chloro-imidazo[1,2-a]pyridin-2-ylmethylsulfanyl)-4-phenyl-imidazol-1-ylamine;
2-(1-Methyl-4-phenyl-1H-imidazol-2-ylmethylsulfanyl)-1H-imidazo[4,5-b]pyridine;
6-Chloro-8-methyl-2-(1-methyl-4-phenyl-1H-imidazol-2-ylsulfanylmethyl)-imidazo[1,2-a]pyridine;
2-[4-(4-Chloro-phenyl)-1-methyl-1H-imidazol-2-ylmethylsulfanyl]-5,7-dimethyl-[1,2,4]triazolo[1,5-a]pyridine;
6-Bromo-7-methyl-2-(1-methyl-4-phenyl-1H-imidazol-2-ylmethylsulfanyl)-[1,2,4]triazolo[1,5-a]pyridine;
2-(Imidazo[1,2-a]pyridin-2-ylmethylsulfanyl)-4-phenyl-imidazol-1-ylamine;
2-(1-Methyl-4-phenyl-1H-imidazol-2-ylsulfanylmethyl)-imidazo[1,2-a]pyridine;
2-(1-Methyl-4-phenyl-1H-imidazol-2-ylmethylsulfanyl)-[1,2,4]triazolo[1,5-a]pyridine-6-carbonitrile;
2-[4-(4-Methoxy-phenyl)-1-methyl-1H-imidazol-2-ylmethylsulfanyl]-5,7-dimethyl-[1,2,4]triazolo[1,5-a]pyridine;
8-Methyl-2-(4-phenyl-1H-imidazol-2-ylsulfanylmethyl)-imidazo[1,2-a]pyridine;
4-(2-(2-((8-chloro-[1,2,4]triazolo[1,5-a]pyridin-2-yl)methylthio)-4-phenyl-1H-imidazol-1-yl)ethyl)morpholine;
8-Methyl-2-[2-(1-methyl-4-phenyl-1H-imidazol-2-yl)-ethyl]-[1,2,4]triazolo[1,5-a]pyridine;
8-Methyl-2-{2-[1-(2-morpholin-4-yl-ethyl)-4-phenyl-1H-imidazol-2-yl]-ethyl}-[1,2,4]triazolo[1,5-a]pyridine;
5-Methyl-2-[2-(1-methyl-4-phenyl-1H-imidazol-2-yl)-ethyl]-[1,2,4]triazolo[1,5-a]pyridine;
5-Methyl-2-{2-[1-(2-morpholin-4-yl-ethyl)-4-phenyl-1H-imidazol-2-yl]-ethyl}-[1,2,4]triazolo[1,5-a]pyridine;
4-(2-(2-((5-chloro-[1,2,4]triazolo[1,5-a]pyridin-2-yl)methylthio)-4-phenyl-1H-imidazol-1-yl)ethyl)morpholine;
5,7-dimethyl-2-(2-(1-methyl-4-phenyl-1H-imidazol-2-yl)ethyl)-[1,2,4]triazolo[1,5-a]pyridine;
4-(2-(2-(5,7-dimethyl-[1,2,4]triazolo[1,5-a]pyridin-2-yl)ethyl)-4-phenyl-1H-imidazol-1-yl)ethyl)morpholine;
6,8-dimethyl-2-(2-(1-methyl-4-phenyl-1H-imidazol-2-yl)ethyl)-[1,2,4]triazolo[1,5-a]pyridine;
5,7-dimethyl-2-(2-(4-phenyl-1H-imidazol-2-yl)ethyl)-[1,2,4]triazolo[1,5-a]pyridine;
2-(2-(1-ethyl-4-phenyl-1H-imidazol-2-yl)ethyl)-5,7-dimethyl-[1,2,4]triazolo[1,5-a]pyridine;
5,7-dimethyl-2-(2-(4-phenyl-1-propyl-1H-imidazol-2-yl)ethyl)-[1,2,4]triazolo[1,5-a]pyridine;
5,8-Dimethyl-2-[2-(1-methyl-4-phenyl-1H-imidazol-2-yl)-ethyl]-[1,2,4]triazolo[1,5-a]pyridine;
5-Methyl-2-[2-(4-phenyl-1H-imidazol-2-yl)-ethyl]-[1,2,4]triazolo[1,5-a]pyridine;
2-[2-(1-Isobutyl-4-phenyl-1H-imidazol-2-yl)-ethyl]-5-methyl-[1,2,4]triazolo[1,5-a]pyridine;
2-[2-(1-Isopropyl-4-phenyl-1H-imidazol-2-yl)-ethyl]-5-methyl-[1,2,4]triazolo[1,5-a]pyridine;
1-Methyl-3-(2-{2-[2-(5-methyl-[1,2,4]triazolo[1,5-a]pyridin-2-yl)-ethyl]-4-phenyl-imidazol-1-yl}-ethyl)-imidazolidin-2-one;
5-Methyl-2-{2-[4-phenyl-1-(3-piperidin-1-yl-propyl)-1H-imidazol-2-yl]-ethyl}-[1,2,4]triazolo[1,5-a]pyridine;
Diisopropyl-(2-{2-[2-(5-methyl-[1,2,4]triazolo[1,5-a]pyridin-2-yl)-ethyl]-4-phenyl-imidazol-1-yl}-ethyl)-amine;
8-Methoxy-2-(1-methyl-4-phenyl-1H-imidazol-2-ylsulfanylmethyl)-[1,2,4]triazolo[1,5-a]pyridine;
5-Methyl-2-{2-[4-phenyl-1-(2-piperidin-1-yl-ethyl)-1H-imidazol-2-yl]-ethyl}-[1,2,4]triazolo[1,5-a]pyridine;
5-Ethyl-2-(1-methyl-4-phenyl-1H-imidazol-2-ylsulfanylmethyl)-[1,2,4]triazolo[1,5-a]pyridine;
8-methoxy-5-methyl-2-(2-(1-methyl-4-phenyl-1H-imidazol-2-yl)ethyl)-[1,2,4]triazolo[1,5-a]pyridine;
8-fluoro-2-(2-(1-methyl-4-phenyl-1H-imidazol-2-yl)ethyl)-[1,2,4]triazolo[1,5-a]pyridine;
8-Ethyl-5-methyl-2-[2-(1-methyl-4-phenyl-1H-imidazol-2-yl)-ethyl]-[1,2,4]triazolo[1,5-a]pyridine, and
5,8-Dimethoxy-2-[2-(1-methyl-4-phenyl-1H-imidazol-2-yl)-ethyl]-[1,2,4]triazolo[1,5-a]pyridine
and pharmaceutically acceptable acid addition salts thereof.

17. A method of treating a subject suffering from a psychiatric disorder, wherein the psychiatric disorder is selected from the group consisting of schizophrenia, schizophreniform disorder, and schizoaffective disorder which method comprises administering a therapeutically effective amount of a compound of claim 1.

18. A pharmaceutical composition comprising a therapeutically effective amount of a compound of claim 1, and one or more pharmaceutically acceptable carriers, diluents and excipients.

19. The method of claim 17, wherein the psychiatric disorder is schizophrenia.

20. The method of claim 17, wherein the psychiatric disorder is schizoaffective disorder.

21. The method of claim 17, wherein the psychiatric disorder is schizophreniform disorder.

22. The method of claim 19, wherein the schizophrenia is of the paranoid, disorganized, catatonic, undifferentiated or residual type.

23. The method of claim 17, wherein the schizoaffective disorder is of the delusional or depressive type.

24. The method of claim 17, wherein the compound is administered in combination with one or more neuroleptic agents.

25. The method of claim 24, wherein the neuroleptic agent is sertindole, olanzapine, risperidone, quetiapine, aripiprazole, haloperidol, clozapine, ziprasidone or osanetant.

26. The compound of claim 10, wherein at least one of $R_2$, $R_3$, $R_4$, $R_5$ and $R_6$ is $C_1$-$C_6$ is methoxy.

27. The compound of claim 11, wherein at least one of $R_2$, $R_3$, $R_4$, $R_5$ and $R_6$ is chlorine or fluorine.

28. The compound of claim 13, wherein at least one of $R_7$, $R_8$ and $R_9$ is methyl.

29. The compound of claim 15, wherein at least one of $R_7$, $R_3$ and $R_9$ is chlorine or bromine.

* * * * *